United States Patent [19]

Clinton et al.

[11] Patent Number: 5,739,140
[45] Date of Patent: Apr. 14, 1998

[54] SELECTED NOVEL ARYL ACRYLICS

[75] Inventors: William P. Clinton; Jim I. McLoughlin, both of St. Louis; Anita E. Otal, Wildwood; John J. Parlow, Arnold; Dennis P. Phillion, St. Charles; Ajit S. Shah, St. Louis, all of Mo.

[73] Assignee: Monsanto Company, St. Louis, Mo.

[21] Appl. No.: 735,600

[22] Filed: Oct. 23, 1996

Related U.S. Application Data

[60] Provisional application No. 60/007,222 Nov. 3, 1995.

[51] Int. Cl.⁶ .................. C07C 251/60; C07C 251/48; A01N 37/50; A01N 37/36; C07D 333/24; C07D 239/52; C07D 233/61

[52] U.S. Cl. .................. 514/269; 514/444; 514/445; 514/447; 514/448; 514/534; 514/538; 514/539; 514/617; 514/618; 514/619; 514/620; 514/621; 514/622; 544/319; 549/59; 549/62; 549/64; 549/65; 549/66; 549/68; 549/70; 549/72; 549/73; 549/77; 549/78; 549/79; 549/80; 560/147; 560/150; 560/152; 560/153; 564/74; 564/78; 564/161; 564/162; 564/164; 564/169

[58] Field of Search ............... 514/513, 508, 514/269, 444, 445, 534, 538, 617, 619; 560/9, 19, 55, 150, 152, 153, 147; 549/59, 62, 64, 65, 66, 68, 70, 72–73, 77–80; 564/161, 162, 164, 169, 74, 78; 544/319

[56] References Cited

U.S. PATENT DOCUMENTS

| | | | |
|---|---|---|---|
| 4,829,085 | 5/1989 | Wenderoth et al. | 514/522 |
| 5,223,526 | 6/1993 | McLoughlin et al. | 514/406 |
| 5,254,717 | 10/1993 | Grammenos et al. | 560/35 |
| 5,371,222 | 12/1994 | Hayase et al. | 544/316 |
| 5,371,223 | 12/1994 | Hayase et al. | 544/316 |
| 5,384,321 | 1/1995 | Kunz et al. | 504/261 |
| 5,395,854 | 3/1995 | Brand et al. | 514/619 |
| 5,407,902 | 4/1995 | Oda et al. | 504/336 |
| 5,486,621 | 1/1996 | Phillion et al. | 549/4 |

FOREIGN PATENT DOCUMENTS

| | | | |
|---|---|---|---|
| 44918/93 | 9/1995 | Australia | C07C 251/60 |
| 0 398 692 A2 | 11/1990 | European Pat. Off. | C07C 251/40 |
| 0 463 488 A1 | 1/1992 | European Pat. Off. | C07C 251/60 |
| 0 499 823 A2 | 8/1992 | European Pat. Off. | C07C 251/48 |
| 0 515 901 A1 | 12/1992 | European Pat. Off. | A61K 31/00 |
| 0 538 231 A1 | 4/1993 | European Pat. Off. | A01N 55/00 |
| 0 633 252 A1 | 1/1995 | European Pat. Off. | C07D 233/61 |
| WO 90/07493 | 7/1990 | WIPO | C07C 251/60 |
| WO 92/13830 | 8/1992 | WIPO | C07C 251/60 |
| WO 94/22844 | 10/1994 | WIPO | C07D 271/06 |
| WO 95/04728 | 2/1995 | WIPO | C07D 273/01 |
| WO 95/15684 | 6/1995 | WIPO | A01N 37/12 |

*Primary Examiner*—Mukund J. Shah
*Assistant Examiner*—Deepak Rao
*Attorney, Agent, or Firm*—Thomas P. McBride; Arnold, White & Durkee

[57] ABSTRACT

Novel compounds of Formula I and methods of making and using the compounds which are useful as fungicides, particularly in the agricultural field:

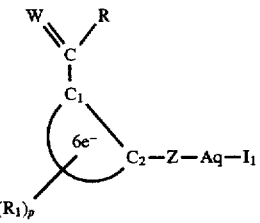

wherein $C_1$ and $C_2$ are carbon atoms which are part of an aromatic ring; W is alkoxyimino, alkoxymethylene or alkylthiomethylene; $R_1$ is independently selected from the group consisting of halogen, cyano, $C_1$–$C_4$ alkyl, $C_1$–$C_4$ alkoxy, wherein the alkyl or alkoxy are optionally substituted by halogen, and p is 0, 1, or 2; Z is —$CH_2$—, —CH(OH)—, —CO—, —O—, —S—, $NR_2$ wherein $R_2$ is hydrogen or a lower aliphatic group, —$CH_2CH_2$—, —CH=CH—,

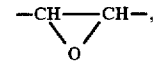

—$CH_2O$—, —$CH_2S$—, —$CH_2S(O)$—, —$OCH_2$—, —$SCH_2$—, —$S(O)CH_2$—, —$CH_2ON$=C($R_3$)— or —CH=NB wherein B is —O—CO—, —N=$CR_3$, or —$CR_3R_4$— wherein $R_3$ and $R_4$ are independently hydrogen or $C_1$–$C_4$ alkyl optionally substituted by halogen;

A is an aromatic moiety having 1–2 aromatic rings connected linearly from Z to $I_1$ wherein the aromatic rings are optionally connected to each other and to $I_1$ in a linear manner with oxygen, nitrogen, or sulfur; q is 0 or 1.

$I_1$ is:

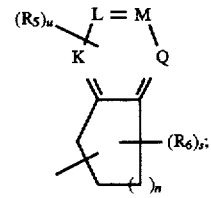

or an agronomically acceptable salt thereof.

69 Claims, No Drawings

SELECTED NOVEL ARYL ACRYLICS

FIELD OF THE INVENTION

The present invention relates to novel oxime ethers and their use as fungicides, particularly in the agricultural field.

BACKGROUND OF THE INVENTION

Various arylalkoxyiminoacetic acid derivatives having utility are known as fungicidal agents. For example, a compound of the formula:

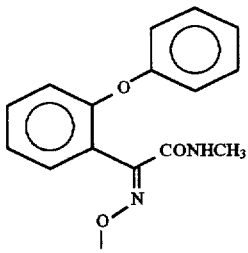

is described in EP 398692. Further a compound of the formula:

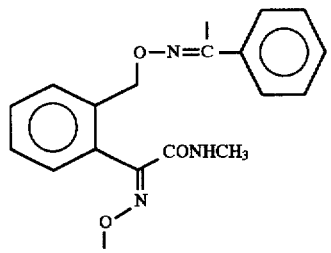

is described in WO92/13830 and EP 463488. Furthermore, a compound of the formula:

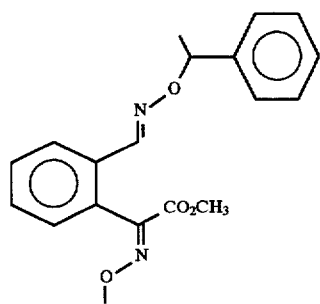

is described in EP 499823. Also, a compound of the formula:

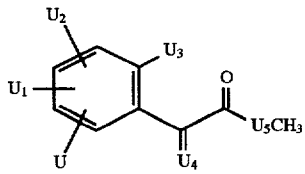

is described in EP 515901. Further, U.S. Pat. No. 4,829,085 discloses other compounds in this class.

Other references of interest are WO 95/04728, EP 0633252A1 and WO 94/22844.

However, none of the disclosed compounds in the above references provide any teaching to the present invention.

SUMMARY OF THE INVENTION

The present invention comprises compounds of Formula I:

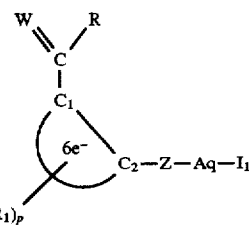

wherein $C_1$ and $C_2$ are carbon atoms which are part of an aromatic ring and are selected from the group consisting of phenyl, thienyl, pyrimidinyl, pyridyl, and pyrazolyl, with the provisos that when the ring is pyrazolyl, pyridyl, or pyrimidinyl, then Z is limited to O or S and that the N of pyrazolyl is substituted by a lower aliphatic group or aryl;

W is alkoxyimino, alkoxymethylene or alkylthiomethylene;

$R_1$ is independently selected from the group consisting of halogen, cyano, $C_1$-$C_4$ alkyl, $C_1$-$C_4$ alkoxy, wherein the alkyl or alkoxy are optionally substituted by halogen, p is 0, 1 or 2;

Z is —CH$_2$—, —CH(OH)—, —CO—, —O—, —S—, NR$_2$ wherein R$_2$ is hydrogen or a lower aliphatic group, —CH$_2$CH$_2$—, —CH=CH—,

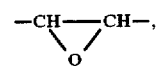

—CH$_2$O—, —CH$_2$S—, —CH$_2$S(O)—, —OCH$_2$—, —SCH$_2$—, —S(O)CH$_2$—, —CH$_2$ON=—C(R$_3$)— or —CH=NB wherein B is —O—CO—, —N=CR$_3$, or —O—CR$_3$R$_4$— wherein R$_3$ and R$_4$ are independently, hydrogen or $C_1$-$C_4$ alkyl optionally substituted by halogen;

A is an aromatic moiety having 1-2 aromatic rings connected linearly from Z to I$_1$ wherein the aromatic rings are optionally connected to each other and to I$_1$ in a linear manner with oxygen, nitrogen, or sulfur; q is 0 or 1. Each aromatic ring is optionally independently substituted by R$_{10}$ groups as defined below. For example, A in Formula I may be expressed as phenyl rings with O, S, or N connecting atoms as follows:

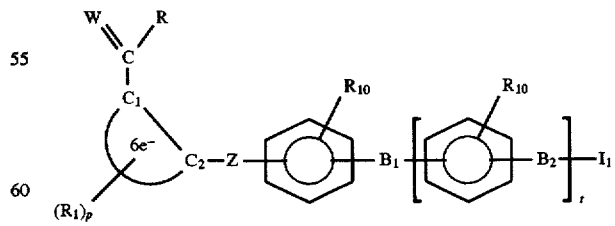

wherein B$_1$ and B$_2$ are O, S or N, the N which optionally substituted with H or $C_1$-$C_4$ alkyl; R$_{10}$ is defined below, and t is an integer from 0 to 1;

Examples of A are aryl, heteroaryl, aryloxy, heteroaryloxy, arylaryl, heteroarylheteroaryl, arylheteroaryl, heteroarylaryl, arylarloxy, aryloxyayl, aryloxyaryloxy, heteroarylheteroaryloxy, heteroayloxyheteroaryl, heteroaryloxyheteroaryloxy, arylheterogyloxy, aryloxyheteroaryl, aryloxyheteroaryloxy, heteroarylaryloxy, heteroaryloxyl, heteroaryloxyaryloxy; other combinations which include sulfur and nitrogen as connecting atoms are also contemplated. Specific examples of A for the aryl ring systems include benzene and naphthalene, and the heteroaryl ring systems include quinoline, isoquinoline, cinnoline, phthalazine, 1,3-benzodiazine, 1,4-benzodiazine, 1,2,4-benzotriazine, benzothiophene, benzofuran, indole, benzimidazole imidazole, benzoxazole, benzothiazole, 1,2-benzisoxazole, 2,1-benzisoxazole, 1,2-benzisothiazole, 2,1-benzisothiazole, pyridine, pyrimidine, pyrimidinyloxyphenyl, pyridazine, pyrazine, 1,3,5-triazine, pyrrole, furan, thiophene, pyrazole, imidazole, oxazole, isoxazole, thiazole, isothiazole, 1,2,4-triazole, 1,2,4-oxadiazole, 1,2,4-thiadiazole, arid tetrazole. Substituent A is preferably a phenol group.

$I_1$ is:

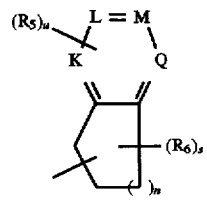

wherein

K, L, M, and Q are independently C or N with the proviso that not more than one or two of K, L, M or Q can be N at once and when K, L, M and Q are carbon each is optionally substituted by $R_5$;

n is 1 or 2 and each $R_5$ and $R_{10}$ group is independently selected from the group consisting of (a) halogen, (b) lower aliphatic group optionally substituted by halogen or $C_1$–$C_4$ alkoxy, (c) $C_1$–$C_4$ alkoxy optionally substituted by halogen, (d) —CN, (e) —$(Y_1)q_1C(=X)(Y_2)_{q2}R_8$, where; X is O or S, $q_1$ and $q_2$ are 0 or 1, $Y_1$ and $Y_2$ are independently selected from the group consisting of O, S, and —$NR_8$; each $R_8$ is independently selected from the group consisting of hydrogen and a lower aliphatic group optionally substituted by halogen or a $C_1$–$C_4$ alkoxy group, wherein $R_8$ cannot be hydrogen if both $q_1$ and $q_2$ are 1 and $Y_2$, is O or S; (f) —$S(O)_rR_9$ where r is 0, 1, or 2, wherein $R_9$ is a lower aliphatic group optionally substituted by halogen or a $C_i$–$C_4$ alkoxy group or $R_9$ is an aryl group optionally substituted by halogen, a $C_1$–$C_4$ alkoxy group, or a $C_1$–$C_4$ alkyl group, (g) —$Si(R_9)_3$, (h) —$C(=NOCH_3)CH_3$, or (i) aryl, aryloxy, arylthio, and arylamino optionally substituted by halogen, $C_1$–$C_4$ alkoxy, or a lower aliphatic group optionally substituted by halogen or $C_1$–$C_4$ alkoxy.

u is an integer from 0 to 4;

$R_6$ is halogen, hydroxy, $C_1$–$C_4$ alkoxy, or a lower aliphatic group, optionally substituted with $C_1$–$C_4$ alkoxy or halogen; s is 0, 1, or 2; and R is:

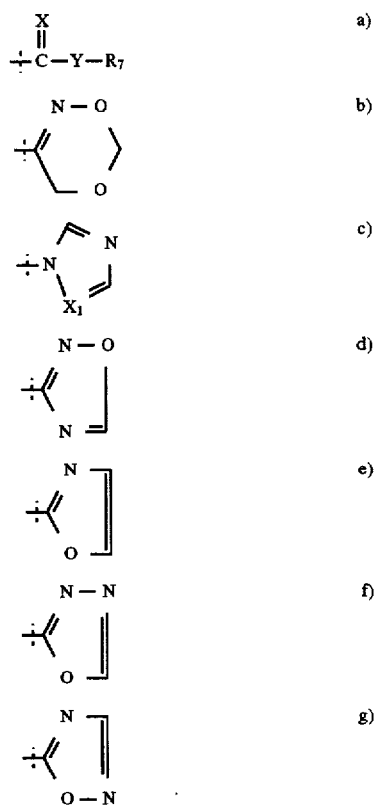

wherein

X is S or O;

Y is a bond, oxygen, sulfur, or nitrogen carrying a hydrogen, a $C_1$–$C_4$ alkyl group or a $C_{1-C4}$ alkoxy group;

each $R_7$ is independently selected from the group consisting of hydrogen and a lower aliphatic group optionally substituted by halogen, hydroxy, or a $C_1$–C4 alkoxy group; and $X_1$ is CH or N;

or an agronomically acceptable salt thereof.

The present invention is also a process for the preparation of a compound of Formula I.

The present invention is also a composition for use as a fungicide comprising a fungicidally effective amount of a compound of Formula I together with an agronomically acceptable carrier.

The present invention is also a method using the compound of Formula I as a fungicidal agent comprising treatment with a fungicidally effective amount of the compound.

DESCRIPTION OF ILLUSTRATIVE EMBODIMENTS

Throughout this application, examples of halogen groups are fluorine, chlorine, bromine and iodine, in particular fluorine and chlorine: examples of the $C_1$–$C_4$ alkyl groups are methyl, ethyl, isopropyl, n-propyl, butyl, tert-butyl, sec-butyl, especially methyl and ethyl, and examples of $C_1$–$C_4$ alkoxy groups are methoxy, ethoxy, propoxy, 2-propoxy, 2-propenoxy, 2-propynoxy, butoxy, 2-butoxy, tert-butoxy, 2-butenoxy, 3-butenoxy, 2-butynoxy, 3-butynoxy, 1-methyl-2-propenoxy, and 1-methyl-2-propynoxy.

A "lower aliphatic group" is defined as an aliphatic group of 1–6 carbons which may be a straight or branched chain with any number of double and triple bonds. Examples of lower aliphatic groups are methyl, ethyl, ethenyl, ethynyl, 1-propyl, 1-methylethyl, 1-propenyl, prop-1-en-2-yl, 2-propenyl, 1-propynyl, 2-propynyl 1-butyl, 2-butyl, 2-methyl-2-propyl, 2-methylpropyl, 1-butenyl, 1-buten-2-yl, 1-buten-3-yl, 3-butenyl, 2-butenyl, 2-buten-2-yl, 2-methyl-2-propenyl, 2-methyl-1-propenyl, 1-butynyl, 2-butynyl, 3-butynyl, 3-butyn-2-yl, 1,3-butadienyl, 1,3-butadien-2-yl, 1-pentyl, 2-pentyl, 3-pentyl, 2-methylbutyl, 3-methylbutyl, 1,1-dimethylpropyl, 1,2-dimethylpropyl, 2,2-dimethylpropyl, 1-pentenyl, 2-pentenyl 3-pentenyl, 4-pentenyl, 1-penten-2-yl, 2-penten-2-yl, 1-methyl-2-butenyl, 1-methyl-3-butenyl, 1-ethyl-2-propenyl, 1-ethyl-1-propenyl, 2-ethyl-1-propenyl, 2-methyl-2-butenyl, 2-methyl-3-butenyl, 3-methyl-1butenyl, 3-methyl-2-butenyl, 3-methyl-3-butenyl, 1,1-dimethyl-2-propenyl, 1-isopropyvinyl, 1,2-dimethyl-1-propenyl, 1,2-dimethyl-2-propenyl, 1-pentynyl, 2-pentynyl, 3-pentynyl, 4-pentynyl, 1-methyl-2-butynyl, 1-methyl-3-butynyl, 1-ethyl-2-propynyl, 2-methyl-3-butynyl, 3-methyl-1-butynyl, 1,1-dimethyl-2propynyl, 1,3-pentadienyl, 1,4-pentadienyl, 2,4-pentadienyl, 1,3 -pentadien-2-yl, 1,4-pentadien-2-yl, 1-methyl-3,1-butadienyl, 1,4-pentadien-3-yl, 1,3-pentadien-3-yl, 2-methyl-1,3 -butadienyl, 3-methyl-1,3-butadienyl, 3-methyl-1,3-butadien-2-yl, 1-hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 1-(isopropyl)-propyl, 1-ethyl-1-methylpropyl, 2,2-dimethylbutyl, 2,3-dimethylbutyl, 3,3-dimethyl-butyl, butyl, 1,1,2-trimethylpropyl, 1,2,2-trimethlpropyl, 1-hexenyl, 2-hexenyl, 3-hexenyl, 4-hexenyl, 5-hexenyl, 1-butylethenyl, 1-methyl-1-pentenyl, 1-methyl-2-pentenyl, 1methyl-3-pentenyl, 1-methyl-4-pentenyl, 1-propyl-2-propenyl, 1-propyl-1-propenyl, 1-ethyl-1-butenyl, 1-ethyl-2-butenyl, 1-ethyl-3-butenyl, 2-methylpentenyl, 2-propyl-2-propenyl, 2-methyl-2-pentenyl, 2-methyl-3-pentenyl, 2-methyl-4-pentenyl, 3-methylpentenyl, 3-methyl-2-pentenyl, 3-ethyl-3-butenyl, 3-methyl-3-pentenyl, 3-methyl-4-pentenyl, 4-methylpentenyl, 4-methyl-2-pentenyl, 4methyl-3pentenyl, 4-methyl-4-pentenyl, 1,1-dimethyl-2-butenyl, 1,1-dimethyl-3-butenyl, 1-(sec-butyl)vinyl, 1,2-dimethylbutenyl, 1-methyl-2-ethyl-2-propenyl, 1,2-dimethyl-2-butenyl, 1,2-dimethyl-3-butenyl, 1-(iso-butyl)vinyl, 1,3-dimethylbutenyl, 1,3-dimethyl-2-butenyl, 1,3 -dimethyl-3-butenyl, 1-ethyl-2-methyl-2-propenyl, 1-ethyl-2-methylpropenyl, 1-(isopropyl)propenyl, 1 -(iso-propyl)-2-propenyl, 1-ethyl-1-methyl-2-propenyl, 2,2-dimethyl-3-butenyl, 2,3-dimethylbutenyl, 2-(iso-propyl)-2-propenyl, 2,3-dimethyl-2-butenyl, 2,3-dimethyl-3-butenyl, 3,3-dimethylbutenyl, 1,1,2-trimethyl-2-propenyl, 1-(tert-butyl) vinyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 1-propyl-2-propynyl, 1-ethyl-2-butynyl, 1-ethyl-3-butynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 1-(iso-propyl)-2-propynyl, 1-ethyl-1-methyl-2-propynyl, 2,2-dimethyl-3-butynyl, 3,3-dimethylbutynyl, 1,3-hexadienyl, 1,4-hexadienyl, 1,5-hexadienyl, 2,4-hexadienyl, 2,5-hexadienyl, 3,5-hexadienyl, 1-methyl-1,3-pentadienyl, 1-methyl-1,4-pentadienyl, 1-methyl-2,4-pentadienyl, 1,4-hexadien-3-yl, 1,5-hexadien-3 -yl, 2,4-hexadien-3-yl, 2,5-hexadien-3-yl, 1-ethyl-1,3-butadienyl, 1,3-hexadien-3-yl, 2-methyl-1,3-pentadienyl, 2-methyl-1,4-pentadienyl, 2-(1-propenyl)-2-propenyl, 2-(2-propenyl)-2-propenyl, 2-methyl-2,4-pentadienyl, 3-methyl-1,3-pentadienyl, 3-ethyl-1,3-butadienyl, 3-methyl-1,4-pentadienyl, 3-methyl-2,4-pentadienyl, 2-(1,3-butadien-2-yl)ethyl, 4-methyl-1,3-pentadienyl, 4-methyl-1,4-pentadienyl, 4-methyl-2,4-pentadienyl, 3-ethyl-1,3-butadien-2-yl, 3-methyl-1,3-pentadien-2-yl, 3-methyl-1,4-pentadien-2-yl, 1,2-dimethyl-1,3-butadienyl, 1-(1,3-butadien-2-yl)ethyl, 4-methyl-1,3-pentadien-2-yl, 4-methyl-1,4-pentadien-2-yl, 1,3-dimethyl-1,3-butadienyl, 2-methyl-1,4-butadien-3-yl, 2-methyl-2,4-pentadien-3-yl, 3-methyl-1,4-pentadien-3-yl, 2,3-dimethyl-1,3-butadienyl, and 2-(isopropenyl)propenyl.

Examples of alkoxyimino, alkoxymethylene or alkylthiomethlene groups for the W substituent in Formula I are $C_1$–$C_4$ alkoxyimino moieties such as methoxyimino, ethoxyimino, n-propoxyimino, isopropoxyimnino, n-butoxyimino, sec-butoxyimino and tert-butoxyimino, preferably methoxyimino; $C_1$–$C_4$ alkoxymethylene moieties such as methoxymethylene, ethoxymethylene, n-propoxymethylene, isopropoxymethylene, n-butoxymethylene, sec-butoxymethylene and tert-butoxymethylene, preferably methoxymethylene; and $C_1$–$C_4$ alkylthiomethylene moieties such as methylthiomethylene, ethylthiomethylene, n-propylthiomethylene, isopropylthiomethylene, n-butylthiomethylene, sec-butylthiomethylene and tert-butylthiomethylene, preferably methylthiomethylene. The preferred group is a $C_1$–$C_4$ alkoxyimino group.

Generally, the compounds of the present invention can be prepared, for example, by methods which are themselves known or are analogous to those described in the chemical literature. In each case the starting materials are also known, commercially available or can be prepared by methods analogous to those described in the literature. Some of the specific methods contemplated are (a) react methyl-2-(bromomethyl)phenyl-2-(methoxyimino)acetate or methyl-3-bromomethyl-2-thienyl-2-(methoxyimino)acetate with one of the following nucleophiles (i) an oxime with a base such as sodium hydride in a solvent such as DMF, (ii) a substituted phenol with a basic salt such as potassium tert-butoxide in a solvent such as THF, or with a basic salt such as potassium carbonate in a solvent such as DMF; or (iii) an alcohol with a base such as tert-butoxide in a solvent such as THF; (b) react methyl 2-[(hydroxyimino)methyl]-α-(methoxyimino)phenylacetate with a base such as sodium hydride in a solvent such as DMF, then with a benzylic bromide; (c) react methyl 2-[2-(iodomethyl)phenyl]-3-methoxypropenoate with substituted phenols and a basic salt such as potassium carbonate in a solvent such as DMF; (d) react methyl 2-[2-(6-chloropyrimidine-4-yloxy)phenyl]-3-methoxypropenoate with substituted phenols and a basic salt such as potassium carbonate in a solvent such as DMF containing a catalyst such as copper (I) chloride; (e) react the methyl esters of Formula I ($R=CO_2CH_3$) with aqueous methylamine or 1-amino-2-propanol to afford amides of Formula I ($R=CONHR_7$); (f) react N-methoxy 2-[4-(1-indanyl)phenoxymethyl]benzenecarboximidoyl chloride with azoles and a base such as sodium hydride in a solvent such as DMF: to produce the compounds of Formula I. Other bases and solvents which would produce the compounds of Formula I are also contemplated.

In addition, compounds of the Formula I, in which Z is —CH=NB wherein B is —O—$CR_3R_4$—and —N=$CR_3$—, can be synthesized by the procedures described as in U.S. Pat. Nos. 5,407,902 and 5,254,717 and the like. Similarly, specific compounds of Formula I in which Z is —$CH_2$ON=C($R_3$)—, can readily be prepared by methods described in AU-A-44918/93. The compounds of the Formula I in which Z is —CH$_2$O— can be synthesized by the procedures as described in U.S. Pat. No. 5,395,854 and the like. The compounds of Formula I for the remainder of the definitions of Z can be synthesized by the procedures analogous to those described in U.S. Pat. No. 5,371,222 or U.S. Pat. No. 5,371,223.

Preparation of compound of the Formula I may result in E/Z isomer or mixtures thereof. If the isomers are required to be separated, this may be accomplished by conventional means. Compounds with the E configuration are particularly preferred.

The compounds of Formula I are suitable as fungicides and for controlling pests such as insects, nematodes and acarids.

The compounds of Formula I have excellent activity against a wide spectrum of fungi which are pathogenic on plants, especially from the classes of Ascomycetes, Oomycetes and Basidiomycetes. Compounds of this invention may have systemic activity and can be employed as leaf and soil fungicides. Compounds of this invention may also be particularly important for controlling a large number of fungi on various crops such as cereals, including wheat, barley and rice; coffee; sugarcane; grapevines; fruit and ornamental plants and vegetables such as cucumbers, beans and pumpkins; and on the seeds of these plants.

The compounds of the present invention are particularly suitable for controlling plant diseases exemplified by the following:

Peronospora species on fruits and vegetables
*Hemileia vastratrix* on coffee
*Erysiphe grainis* on cereals
Erysiphe species on vegetables, fruits, and ornamentals
Sphaerotheca species on vegetables
Monilinia species on fruits, vegetables, and ornamentals
*Uncinula necator* on grapes
Puccinia species on cereals
Rhizoctonia species on cereals, turf, and rice
Ustilago species on cereals
Tilletia species on cereals
Pyrenophora species on cereals
Mycosphaerella species on cereals and bananas
Gaemannomyces on cereals
*Venturia inaequalis* on apples
Ustilago species on cereals
*Leptosphaeria nodorum* on cereals
*Botrytis cinema* on fruits and vegetables
*Pseudocercosperella herpotrichoidcs* on cereals
*Pyricularia oryzae* on rice
Phytophthora species on fruits, vegetables, tobacco, and ornamentals
Verticillium species on fruits, vegetables, and ornamentals
*Plasmopora viticola* on grapes
Fusarium species on cereals, fruits, and vegetables
*Microdochium nivale* on cereals
Alternaria species on fruits and vegetables
Pythium species on fruits, vegetables and turf.

The compounds are applied by treating the fungi or the plants, seeds, materials or soil to be protected from fungal attack with a fungitidal amount of the active ingredients. The application is carried out before or after infection of the materials, plants or seeds by the fungi.

The compounds of Formula I are also suitable for controlling pests from the classes of insects, acarids and nematodes. They can be employed as pesticides in crop protection and in the hygiene, store protection and veterinary sectors.

The compounds of the present invention may be used as is without adding any other components, but generally, they are formulated into emulsifiable concentrates, wettable powders, suspension formulations, granules, dusts, and the like by mixing with a solid or liquid carrier, a surface active agent and other adjuvants for formulation. The compounds of the present invention may also be microencapsulated or otherwise formulated for delayed release of activity.

The content of a compound of the present invention contained as an active ingredient in these formulations is 0.1 to 99.9%, preferably 0.2 to 80% by weight, and more preferably 2 to 50% by weight. The concentration of the active compound in the spray solutions as they are applied to growing plants will be much less, from about 1 to about 1000, preferably from about 10 ppm up to about 1000 ppm.

The exact amount of active ingredient per hectare to be employed in the treatment or prevention of disease is dependent upon various factors, including the plant species and stage of development of plants and disease, the amount of rainfall, and the specific adjuvants employed. In foliar applications a dosage from about 1 to about 2000 g/ha, preferably from about 20 to about 250 g/ha, is usually employed. In soil applications a dosage from about 1 to about 2000 g/ha, preferably from about 50 to about 500 g/ha is usually employed. Lower or higher rates may be required in some instances. When the active ingredient is used for treating seed, rates of 0.0005 to 100 g per Kg of seed, preferably from 0.01 to 50 g per Kg of seed is employed. One skilled in the art can readily determine from this specification, including the following examples, the optimum rate to be applied in any particular case.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide, and the like. The liquid carrier includes, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cottonseed oil and the like, dimethyl sulfoxide, acetonitrile, water, and the like.

The surface active agents used for emulsification, dispersion, wetting, etc., include, for example, anionic surface active agents, such as salts of alkyl sulfate, alkyl or aryl sulfonates, dialkylsulfo-succinates, salts of polyoxyethylene alkyl aryl ether phosphoric acid esters, or naphthalenesulfonic acid/formalin condensates, etc., and nonionic surface active agents, such as polyoxyethylene alkyl ether, polyoxyethylenepolyoxypropylene block copolymers, sorbitan fatty acid esters, or polyoxyethylene sorbitan fatty acid esters, etc. Other adjuvants for formulation include, for example, xanthan gum, lignosulfonates, alginates, polyvinyl alcohol, gum arabic, and CMC (carboxymethyl cellulose).

Penetrating agents, to increase systemic activity may also be added to the compounds of the present invention. When used in plant protection, a compound according to the invention or mixtures thereof, as such or in their formulations, can also be used in the form of mixture with other active ingredients, for example, herbicides, bactericides, acaricides, nematocides, insecticides, growth regulators, other fungicides and compounds identified as synergists, and may furthermore be mixed and applied together with fertilizers. The mixtures are advantageous, for example to broaden the spectrum of action or to prevent the build-up of resistance. In some cases, synergistic effects are observed, which means that the activity of the mixture is greater than the total of the activities of the individual components.

Examples of fungicides which may be combined with the novel compounds are: 2-aminobutane; 2-anilino-4-methyl-6-cyclopropylpyrimidine; 2',6'-dibromo-2-Methyl-4'trifluoromethoxy-4'-trifluoromethyl-1,3-thiazol-5-carboxanilide; 2,6-dichloro-N-(4-trifluoromethylbenzyl) benzamide; (E)-2-methoxyimino-N-methyl-2-(2-phenoxyphenyl)acetamide; 8-hydroxyquinoline sulphate: methyl (E)-2-{2-[6(2-cyanophenoxy)pyrimidin-4-yloxy] phenyl]-3-methoxyacylate: methyl (E)-methoximino{alpha (o-tolyloxy)-o-tolyl]acetate; 2-phenytphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprodinil, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, foxetyl-aluminium, fthalide, fuberidazole, furalaxyl, furmecyclox, guazatine, hexachlorobenzene, hexaconazole, hymexazole, imazalil, imibenconazole, iminoctadine, iprobentfor (IBP), iprodione, isoprothiolane, kasugamycin, copper preparations, such as: copper hydroxide, copper naphthenate, copper oxychloride, copper sulphate, copper oxide, oxine copper and Bordeaux mixture, mancopper, mancozeb, maneb, mepanipyhrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, perfurazoate, penconazole, pencycuron, phosdiphen, pimaricin, piperalin, polyoxin, probenazole, prochloraz procymidone, propamocvarb, propiconazole, propineb, pyrazophos, pyrifenox, pyrimethanil, pyroquilon, quintozen (PCNB), sulphur and sulphur preparations, tebuconazole, tecloftalam, tecnazen, tetraconazole, thibendazole, thicyofen, thifluzimide, thiophanate-methyl, thiram, tolclophosmethyl, tolyifluanid, triadimefon, triadimenol, triazoxide, trichlamide, tricyclazole, tridemorph, triflumizole, triforine, triticonazole, validamycin A, vinclozolin, zineb, ziram and the compounds described as the invention in EP 0538231, U.S. application Ser. No. 08/356,770, U.S. Pat. No. 5,223, 526, PCT US95/11219, PCT US95/11439, PCT US95/11436, PCT US95/11301, and PCT US95/11438.

Additionally, the present invention compounds may also be combined with compounds which enhance the natural resistance of plants such as are described in U.S. Pat. No. 5,384,321 or WO 95/15684.

Examples of bactericides which may be combined with the novel compounds of the present invention are: Bronopol, dichlorophen, nitrapyrin, nickel dimethyldithiocarbamate, kasugamycin, octhilinon, furanecarboxylic acid, oxytetracyclin, probenazole, streptomycin, tecloftalam, copper sulphate and other copper preparations.

Examples of insecticides, acaricides and nematicides which may be combined with the novel compounds of the present invention are: Abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betasyluthrin, bifenthrin, BPMC, brofenprox, bromophos A, bufencarb, buprofezin, butocarboxin, butylpyridaben, cadusafox, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, cloflentezine, cyanophos, cycloprothrin, cyfluthrin, cyhalothrin, cyhexatin, cypermethrin, cyromazine, deltamethrin, demeton M, demeton S, demeton-S-methyl diafenthiuron, diazinon, dichlofenthion, dichlorvos, dicliphos, dicrotophos, diethione, diflubenzuron, dimethoate, dimethylvinphos, dioxathion, disulphoton, edifenphos, emamectin, esfenvalerate, ethiofencarb, ethione, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fiucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathione, ivermectin, lambdacyhalothrin, lufenuron, malathion, mecarbam, meavinphos, mesulphenphos, metaldehyde, methacrifos, methamidophos, methidathion, methiocarb, methomyl metolcarb, milbemectin, monocrotophos, moxidectin, naled, NC 184, NI 25, nitenpyram, ometboate, oxamyl, oxydemethon M, oxydeprofos, parathion A, parathion M, permethrin, phenthoate, phorate, phosalone, phosmet, phospham; don, phoxim, pirimicarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulphotep, sulprofos, tebufenozid, tebufenpyrad, tebupirimphos, teflub enzuron, tefluthrin, temephos, terbam, terbufos, tetrachlorvinphos, thiafenox, thiodicarb, thiofanox, thiometon, thionazin, thuringiensin, tralomethrin, triarathen, triazophos, triazuron, trichlorfon, triflumuron, trimethacarb, vamidathio, XMC, xylylcarb, zetamethrin.

PREPARATION EXAMPLES

The following examples are illustrative of the present invention and are not meant to be limiting thereto. Abbreviations have the meanings shown:

| | |
|---|---|
| ha | hectare |
| Kg | kilogram |
| g | gram |
| RT | room temperature |
| RH | relative humidity |
| HPLC | chromatography on silica (Waters 500 A preparative liquid chromatograph) |
| DMF | dimethylformamide |
| mL | milliliter |
| DMSO | dimethylsulfoxide |
| m/v | material per volume |
| v/v | volume per volume |
| ave | average |

EXAMPLES OF USE

Typical biological data indicating the excellent fungicidal activity of the compounds of the invention obtained using the bioevaluation in vitro assay method of Example 1 and the bioevaluation in vivo assay methods of Examples 2–6.

Example 1

Microdochium nivale Spore Germination Inhibition

Water agar with 1.5% agar (m/v) is heated on a hot plate to melting and dispensed into 50 mL erlenmeyer flasks with 10 mL. of agar per flask. One flask is required for each treatment in the treatment list. These are then autoclaved to sterilization. When the molten agar is cool enough to begin pouring, approximately 55° C., the test compounds in solvent are dispensed into the agar to achieve the desired final concentration described in the Table. The agar to solvent ratio is 1000:1 v/v. After adding the material and solvent the agar is gently agitated, and poured into a petri plate.

Commercial and internal standards included in each test are incorporated in the same manner as the experimental compounds.

After the agar has cooled and solidified the plates are ready for inoculation. A conidial suspension of the fungus, Microdochium nivale, is prepared with roughly 20,000 spores/mL of sterile distilled water. Three drops of this suspension are dispensed onto each plate equidistantly in a triangular pattern. The plates are then incubated at 21° C. for 20 hours. At that time the germ tubes should be sufficiently long enough to measure using an ocular lens scale on a microscope. Several germ tubes in each inoculum drop are measured to determine the average amount of growth. This procedure is then repeated for the other two drops. The average of the three inoculum drops is then used in the following equation to determine the effectiveness of each treatment.

Inhibition=100-[(ave. treatment length/ave. control length)×100]

Example 2

Barley Powdery Mildew Protectant Methods

The following describes the procedures and methods used in the barley powdery mildew foliar assay.

A) Pathogen/Inoculum Production

The barley powdery mildew fungus, *Erysiphe graminis f. sp. hordei*, is maintained continuously on barley seedlings in an isolated, environrnmentally controlled growth chamber.

B) Host Propagation

Barley seedlings, cv. Perry, are grown to the second leaf stage in a growth chamber set at 21° C., 80% RH with a 12 hour photoperiod.

C) Test Compound Preparation

1) Experimental compounds

The compounds were applied at 20 and 5 ppm. Formulation is generally in 20% acetone, 79.95% water, and 0.05% Tween® 20. Three pots (with 3 plants/pot) are utilized per treatment rate. The application volume is 2 mL per treatment. Formulated materials/products are brought up to the appropriate treatment volume with water containing 0.05% Tween® 20, v/v.

2) Controls and standards:

The commercial standard used is Alto® (active ingredient cyproconazole) at the rate of 20 and 5 ppm. A set of control plants, treated with the formulation blank and inoculated, are also included.

D) Compound Application

Compound is sprayed onto the leaves of the plants (pots positioned on a rotating table) using a DeVilbiss Model 152 hand sprayer. Coverage of the first leaf is essential. After the plants have thoroughly dried they are returned to the growth room and randomized.

E) Inoculation/Incubation

Twenty four hours later the treated plants are removed to a "mildew chamber38 and inoculated by gently brushing their leaves with the leaves of a previously infected plant with actively sporulating mildew pustules. The mildew incubation chamber settings are identical to that of the host propagation chamber (see above).

F) Evaluation

The test is assessed 6–7 days after inoculation. Treatments are evaluated by visually estimating the percentage of tile leaf area infected on the first leaf. Three ratings are made on each pot (replicate). Phytotoxicity and growth effects are also noted and recorded at this time.

G) Data Handling

Treatment means are calculated and percent disease control is determined by the formula:

%Control=(control mean−treatment mean)×100/control mean

The inoculated control treatment mean is used for this calculation.

Example 3

Barley Powdery Mildew Curative Methods

This method is conducted as in Example 2 above with the following exception: Plants are inoculated as described and then 24 hours later the incubation period is temporarily interrupted for chemical treatment.

Example 4

Wheat Glume Blotch Foliar Assay Methods

A) Pathogen/Inoculum Production

The wheat glume blotch fungus, *Leptosphaeria nodorum*, is maintained in the pycnidial state on yeast malt agar (YMA) at 20° C., 12 hour photoperiod.

Test inoculum is prepared by flooding seven day old culture plates with deionized water amended with Tween® 20 (0.1% v/v) and gently scraping the pycnidia to release the extruding masses of conidia. The resulting spore suspension is filtered through two layers of cheese cloth and adjusted to $4 \times 10^6$ spores/mL utilizing the Tween® 20 solution.

B) Host Propagation

Winter wheat plants, cv. Caldwell, are grown in 5.7 cm$^2$ pots, three per pot, and maintained in a growth chamber set at 20° C., 80% RH with a 12 hour photoperiod.

C) Test Compound Preparation

1) Experimental compounds:

Compounds are most commonly applied at the dose rate of 20 ppm. Formulation is generally in 20% acetone, 79.95% water, and 0.05% Tween® 20 Three pots (with 3 plants/pot) are utilized per treatment rate. Application volume is 3 mL/treatment. Formulated commercial products are diluted to the appropriate treatment volume with water containing 0.05% Tween® 20, v/v.

2) Controls and standards:

The commercial standard used is Horizon® (active ingredient tebuconazole) at the rate of 20 ppm. A set of control plants, treated with a formulation blank and inoculated, are also included.

D) Compound Application

Seedlings are sprayed at the two-leaf stage (GS 12) using a DeVilbiss Model 152 hand operated sprayer set at 15–20 psi. Coverage of the first leaf is essential. The plants are allowed to dry, returned to the growth room, and randomized.

E) Inoculation/Incubation

Twenty four hours after compound application and prior to inoculation, the test plants are preconditioned for at least one hour in a dark growth chamber set at 20° C. and 100% RH. After the preconditioning period is over, the prepared conidial suspension is applied to run-off using a DiVilbiss hand operated sprayer. The plants are then returned to the preconditioning chamber and incubated at the same settings for 96 hours. Light is supplied to the plants during the last twelve hours of incubation. At the end of the 96 hour period, the plants are returned to the environmental conditions under which they were grown.

F) Test Evaluation

Eight to ten days after removal from the high humidity chamber, or twelve to fourteen days after inoculation, treatments are evaluated by visually estimating the percentage of the leaf area (on the first leaf) covered with lesions. Three ratings are made on each pot which constitutes a replicate.

G) Data Handling

As per "Barley Powdery Mildew Assay Methods" in Example 2.

Example 5

Wheat Leaf Rust Protectant Methods

The methods for conducting this assay are the same as those described for Example 2 with the following exceptions:

Wheat variety "Caldwell" is seeded into 5.7 cm pots containing a commercial potting soil and grown in a growth chamber with 21° C. ambient temperature and a 12 hour light cycle. At application time the plants should have one fully formed leaf, and there should be at least three plants per pot.

Then one day following compound application, the plants are inoculated with the pathogen, *Puccinia recondita*. To inoculate a test, urediospores are dislodged from previously infected inoculum plants onto the foliage of the test plants, and the plants are placed in a mist tent for 24 hours at 20° C. in the dark. The test can then be returned to the previous growing conditions until foliar symptoms are evident and the plants can be assessed.

Example 6

Vine Downy Mildew Protectant Methods

The procedures and methods used in the foliar vine downy mildew disease assay are as follows:

A) Pathogen/Inoculum Production

The vine downy mildew fungus is an obligate parasite and must be maintained on a living host. Vine seedlings are infected each week with a spore suspension of P. viticola in order to provide spores for assay.

B) Host Propagation

Grape seedlings, variety "Carignane", *Vitus vinifera*, are grown from seed. The seedlings are maintained under a shade cloth in an environmentally controlled greenhouse. Plants are ready for assay when they have two to three fully expanded leaves.

C) Test Compound Preparation

1) Experimental compounds:

The compounds were applied at 20 and 5 ppm. Formulation is generally in 20% acetone, 79.95% water, and 0.05% Tween® 20. Three pots (with one plant/pot) are utilized per treatment rate. The application volume is 2 mL per treatment. Formulated materials/products are brought up to the appropriate treatment volume with water containing 0.5% Tween 20, v/v.

2) Controls and standards:

The commercial standard used is Ridomil® (active ingredient metalaxyl) at the rate of 20 and 5 ppm. A set of control plants, treated with the formulation blank and inoculated, are also included.

D) Compound Application

Compound is sprayed onto the upper and lower surfaces of the second and third leaf of each plant. The plants are returned to the growth room after they have dried, and randomized.

E) Inoculation/Incubation

Treated vines are inoculated 24 hours after chemical applications. A 20,000/mL spore suspension is applied to the lower surface of the leaves. Inoculated plants are placed in a dark dew chamber set at 20° C. for 24 hours. Following the initial incubation, the plants are moved to a growth chamber set at 21° C., 85% RH with a 12 hour photoperiod.

F) Evaluation

The test is assessed 6–7 days after inoculation. Prior to disease assessment, the treated plants are placed in a dew chamber overnight to allow spores to develop on the underside of the leaves. Infection level is then evaluated by visually estimating the percentage of the leaf underside covered with spores. Phytotoxicity and growth effects are also noted and recorded at this time.

G) Data Handling

Treatment means are calculated and percent disease control is determined by the formula: "(control mean–treatment mean) times 100/control mean". The inoculated control treatment mean is used for this calculation.

SYNTHESIS OF INTERMEDIATES

1-Indanol, 2-indanol, β-Tetralol, and 4-(1-indanyl)phenol were purchased from commercial sources. 2-(4-Bromophenyl)-2-methyl-1,3-dioxolane, methyl 2-(bromomethyl)benzoate, methyl-2-(bromomethyl)phenyl-2-(methoxyimino)acetate, methyl-3-bromomethyl-2-thienyl-2-(methoxyimino)acetate, 4-(1-tetralinyl)phenol, methyl 2-[2-(chloromethyl)phenyl]-3-methoxypropenoate, methyl 2-[(hydroxyimino)methyl]-α-(methoxyimino) phenylacetate, and methyl 2-[2-(6-chloropyrimidine-4-yloxy)phenyl]-3-methoxypropenoate were prepared according to published literature procedures. The compounds of intermediates a-aa showed satisfactory spectral data.

Examples 7–16 illustrate the synthesis of those intermediates for which methods for synthesis are not available in the literature.

Example 7

Method A: Synthesis of Intermediates a–d

A solution of n-butyllithium in hexanes (1 equiv) was added dropwise to a dry-ice/acetone cooled solution of 2-(4-bromophenyl)-2-methyl-1,3-dioxotane (1 equiv) in THF. The resulting solution was stirred at −78° C. for 1h then a solution of a ketone (1 equiv) in THF was added to this cold solution of aryl lithium. The reaction was allowed to warm to room temperature, quenched with saturated aqueous ammonia chloride, and extracted with ether. The organic solution was dried over magnesium sulfate and the product purified by chromatography over silica gel eluted with ethyl acetate/hexane mixtures.

The product of the above reaction was mixed with excess aqueous 2N HCl, and enough acetone added to effect solution. A catalytic amount of para-toluene sulfonic acid was added and the solution was refluxed for 1 d to hydrolyze the ketal and dehydrate the benzylic carbinol. The reaction was concentrated to remove most of the acetone, then was extracted with ether. The organic extract was washed with brine, dried over magnesium sulfate, and the product purified by chromatography over silica gel eluted with ethyl acetate/hexane mixtures.

A solution of the above olefin in ethanol or ethyl acetate was hydrogenated over a catalytic mount of 5–10% Pd/C in a Parr hydrogenation apparatus. Selective reduction of the olefin over the ketone could be achieved with short reaction times. Overnight hydrogenation saturated the olefin and reduced the ketone to the alcohol. The reaction was filtered through celite, concentrated and purified by chromatography over silica get eluted with ethyl acetate/hexane mixtures. Intermediates a–d were prepared as intermediates using Method A.

Intermediate a, 4-(1-indanyl)acetophenone

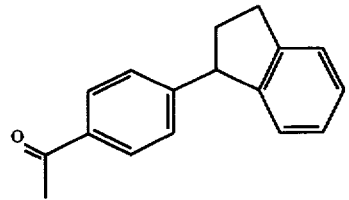

Intermediate b, 1-(1-hydroxyethyl)-4-(5-methoxy-1-indanyl)benzene

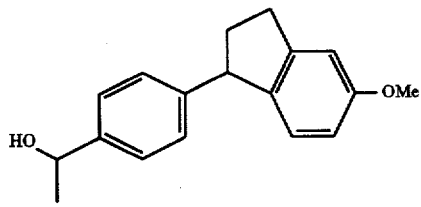

Intermediate c, 1-(1-hydroxyethyl)-4-(1-tetralinyl)benzene

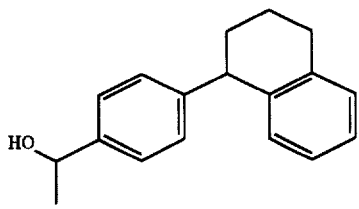

Intermediate d, 4-(5-methoxy-1-tetralinyl)acetophenone

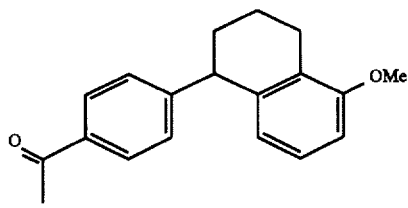

Example 8

Method B: Synthesis of intermediates e and f

Manganese dioxide (5 equiv) was added to a benzene solution of a benzylic alcohol from method A. The mixture was refluxed for 1h, then was filtered through celite and concentrated to afford the crude ketone.

Intermediates e–f were prepared as intermediates using Method B.

Intermediate e, 4-(5-methoxy-1-indanyl)acetophenone

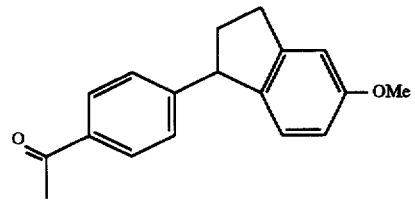

Intermediate f, 4-(1-tetralinyl)acetophenone

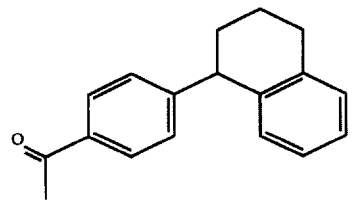

Example 9

Method C: Synthesis of Intermediates g–j

A mixture of the acetopheone (1.0 equiv) from method A or B, hydroxylamine hydrochloride (1.25 equiv), and sodium acetate (1.25 equiv) was refluxed in methanol overnight to form the oxime. The resulting reaction mixture was concentrated to remove most of the methanol, then the residue was partitioned between ethyl acetate and water. The organic portion was washed with brine, dried over magnesium sulfate, and, if necessary, purified by chromatography over silica gel with ethyl acetate/hexane mixtures.

Intermediates g–j were prepared as intermediates using Method C.

Intermediate g. 4-(1-indanyl)acetophenone oxime

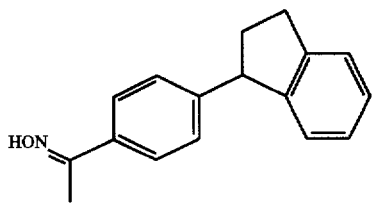

Intermediate h. 4-(5-methoxy-1-indanyl)acetophenone oxime

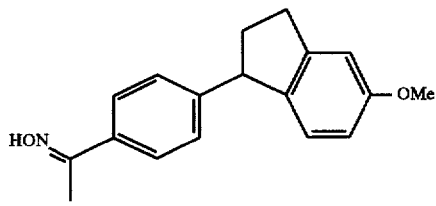

Intermediate i. 4-(1-tetralinyl)acetophenone oxime

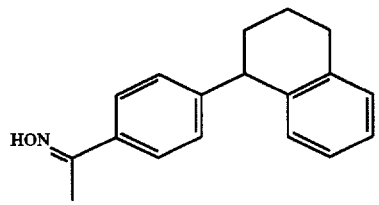

Intermediate j. 4-(5-methoxy-1-tetralinyl)acetophenone oxime

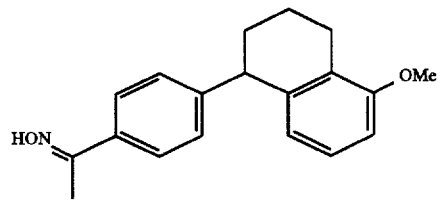

Example 10

Method D: Synthesis of Intermediates k–o

A solution of a substituted indanone (1.0 equiv) in THF was added dropwise to an ice water cooled 0.5M solution of 4-anisyl magnesium bromide (1.0 equiv) in THF. The reaction was allowed to stir at room temperature overnight, then was quenched with aqueous ammonium chloride and partitioned between ether and water. The organic phase was dried over magnesium sulfate and concentrated to afford the crude carbinol.

The carbinol was dissolved in acetone and dehydration effected by adding aqueous 5% HCl to the cloud point. This was refluxed for 1h, then was stripped under vacuum and purified by chromatography over silica gel with ethyl acetate/hexane mixtures.

A solution of the olefin in ethyl acetate was hydrogenated over catalytic 5% Pd/C in a Parr apparatus. The reaction was then filtered through celite, concentrated, and purified by chromatography over silica gel eluted with ethyl acetate/hexane mixtures or recrystallization from hexanes.

A 1M solution of boron tribromide (1.2 equiv) in methylene chloride was added dropwise to an ice water cooled solution of this reduced O-methyl phenol (1.0 equiv) in methylene chloride. The cooling bath was removed and the resulting reaction was stirred overnight at room temperature. The reaction was quenched by pouring over ice and separating the layers. The methylene chloride phase was dried over magnesium sulfate, concentrated, and the product purified by reverse phase chromatography or recrystallization from hexanes.

Intermediates k–o were prepared as intermediates using method D.

Intermediate k. 4-(5-chloro-1-indanyl)phenol

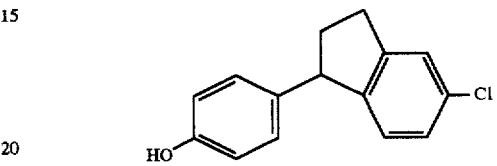

Intermediate l. 4-(5-fluoro-1-indanyl)phenol

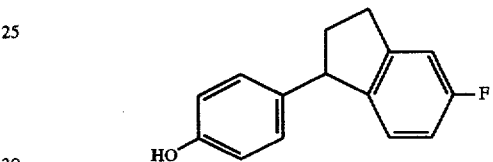

Intermediate m. 4-(2-methyl-1-indanyl)phenol

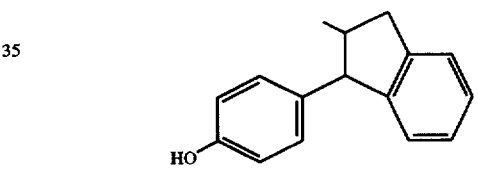

Intermediate n. 4-(3-methyl-1-indanyl)phenol

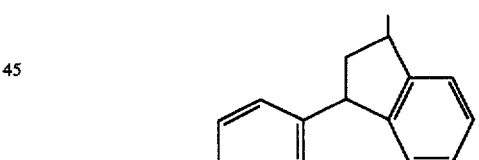

Intermediate o. 4-(4-methyl-1-indanyl)phenol

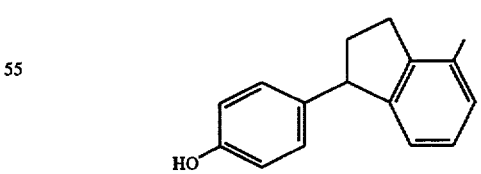

Example 11

Synthesis of intermediate p

An 0.5M solution of 4-anisyl magnesium bromide in THF (66.7 mL. 33.3 mmol) was added dropwise to an ice-water cooled solution of benzyl acetone (5.0 mL. 33.3 mmol) in THF. The resulting reaction was allowed to warm to room temperature, and after 1h was partitioned between aqueous ammonium chloride and ether. The organic phase was dried over magnesium sulfate, concentrated, and purified by chromatography over silica gel eluted with 1:5 ethyl acetate/hexanes to afford 6.2 g of 4-(1-hydroxy-4-phenyl-2-butyl) anisole as a clear oil.

A mixture of 4-(1-hydroxy-4-phenyl-2-butyl) anisole (5.92 g, 23.1 mmol) in excess polyphosphoric acid was stirred at room temperature for 2h, then poured into ice-water and extracted with ether. The organic phase was dried over magnesium sulfate, concentrated, and purified by chromatography over silica gel eluted with 5% ethyl acetate in hexanes to afford 2.12 g of 4-(1-methyl-1-indanyl) anisole as a yellow oil.

A 1M solution of boron tribromide (10.0 mL, 10.0 mmol) was added dropwise to an ice-water cooled solution of 4-(1-methyl-1-indanyl) anisole (2.1 g, 8.8 mmol) in methylene chloride. The cooling bath was removed and the resulting reaction was stirred at room temperature overnight. The reaction was quenched by pouring over ice and separating the layers, then the methylene chloride phase was washed with brine, dried over magnesium sulfate, concentrated, and purified by chromatography over silica gel eluted with 15% ethyl acetate in hexanes to afford 1.73 g of 4-(1-methyl-1-indanyl)phenol as a light green oil.

Intermediate p. 4-(1-methyl-1-indanyl)phenol

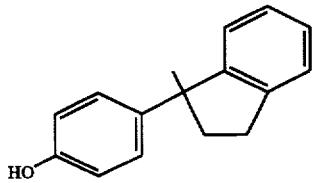

Example 12

Synthesis of Intermediate q

3-Phenyl-1-1-propyl magnesium bromide was prepared from the reaction of 3-phenyl-1-bromopropane (8.0 mL, 52.6 mmol) and magnesium turnings (1.40 g, 57.6 mmol) in THF. This solution was added dropwise to an ice-water cooled solution of 3-methyl-para-anisaldehyde (7.70 mL, 52.6 mmol) in THF. The resulting reaction was allowed to warm to room temperature, and after 1h was partitioned between aqueous ammonium chloride and ether. The organic phase was dried over magnesium sulfate, concentrated, and purified by chromatography over silica gel eluted with 15% ethyl acetate in hexanes to afford 8.35 g of 2-methyl-4-(1-hydroxy-4-phenyl-1-butyl) anisole as a clear oil.

A 1M solution of titanium tetrachloride in toluene (74.1 mL, 74.1 mmol) was added dropwise to a solution of 2-methyl-4-(1-hydroxy-4-phenyl-1-butyl) anisole (5.0 g, 18.5 mmol) in methylene chloride. The mixture was stirred at room temperature for 3h, then the reaction was quenched by pouring into excess aqueous saturated sodium bicarbonate. After stirring for 5 min the mixture was extracted with ether, and the organic phase was dried over magnesium sulfate, concentrated, and purified by chromatography over silica gel eluted with hexanes to afford 2.46 g of 2-methyl-4-(1-tetralinyl) anisole as a clear oil.

A 1M solution of boron tribromide (10.7 mL, 10.7 mmol) was added dropwise to an ice-water cooled solution of of 2-methyl-4-(1-tetralinyl) anisole (2.46 g, 9.7 mmol) in methylene chloride. The cooling bath was removed and the resulting reaction was stirred at room temperature overnight. The reaction was quenched by pouring over ice and separating the layers, then the methylene chloride phase was washed with brine, dried over magnesium sulfate, concentrated, and purified by chromatography over silica gel eluted with 15% ethyl acetate in hexanes of 2-methyl-4-(1-tetralinyl) phenol as an oil.

intermediate q. 2-methyl-4-(1-tetralinyl)phenol

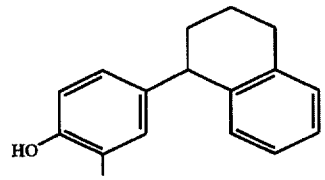

Example 13

Method E: Synthesis of Intermediates r–w 1,1'-(Azodicarbonyl)dipiperidine (1.0 equiv) was added to an ice-water cooled solution of a secondary alcohol (1.0 equiv), 3- or 4-hydroxyphenyl benzoate (1.0 equiv), and triphenylphosphine (1.0 equiv) in THF. After 10 min the reaction was allowed to warm to room temperature and stir overnight. Hexanes were added and the slurry was filtered to remove the solid by-products which had precipitated. The filtrate was then concentrated and purified by chromatography over silica gel eluted with ethyl acetate/hexane mixtures to give the 3- or 4-alkoxyphenyl benzoate.

Aqueous 5% sodium hydroxide (0.7 volumes) was added to an 0.2M solution of the 3- or 4-alkoxyphenyl benzoate in 1,4-dioxane (1 volume). The resulting mixture was stirred overnight at room temperature, then was partitioned between ether and water. The organic phase was washed with water and dried over magnesium sulfate, then was concentrated and purified by crystallization from ether/hexanes or by chromatography over silica gel eluted with ethyl acetate/hexane mixtures to give the 3- or 4-alkoxyphenol.

Intermediates r–w were prepared as intermediates using method E.

Intermediate r. 4-(1-indanoxy)phenol

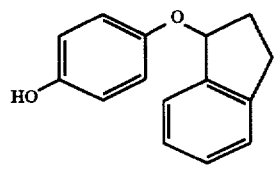

Intermediate s. 4-(2-indanoxy)phenol

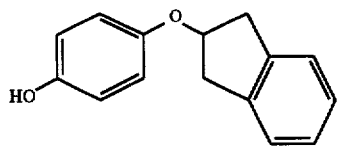

21

Intermediate t, 4-(2-tetralinoxy)phenol

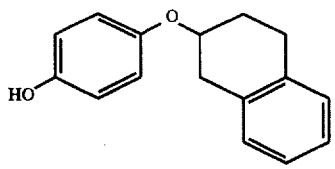

Intermediate u, 3-(1-indanoxy)phenol

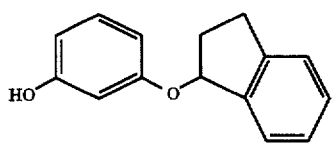

Intermediate v, 3-(2-indanoxy)phenol

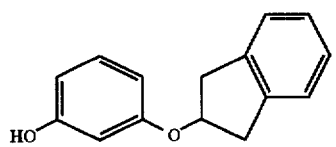

Intermediate w, 3-(2-tetralinoxy)phenol

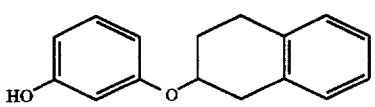

Example 14

Synthesis of Intermediate x

Sodium borohydride (321 mg, 8.4 mmol) was added in portions to an ice-water cooled solution of 4-(1-indanyl) acetophenone (intermediate a, 1.00 g, 4.2 mmol) in methanol. After 3 hours the reaction was quenched by the careful addition of excess aqueous 3% HCl, then was concentrated under vacuum to remove the methanol. The residue was diluted with ether and washed with water followed with brine, then was dried over magnesium sulfate, concentrated, and purified by chromatography over silica gel eluted with 1:4 ethyl acetate:hexanes to afford 600 mg (61%) of 1-(1-hydroxyethyl)-4-(1-indanyl)benzene as a colorless oil.
Intermediate x, 1-(1-hydroxyethyl)-4-(1-indanyl)benzene

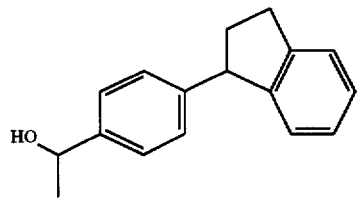

Example 15

Method F: Synthesis of Intermediates y and z

Pyridine (2 equiv) was added dropwise to an ice-water cooled solution of phosphorus tribromide (3 equiv) in benzene. To this solution was added a solution of intermediate x or b (3 equiv) and pyridine (1 equiv) in benzene. The resulting reaction mixture was allowed to warm and stir at room temperature overnight, then was quenched by pouring into icy water and extracting with ether. The organic phase was washed with brine and dried over magnesium sulfate, then was concentrated and purified by chromatography over silica gel eluted with ethyl acetate/hexane mixtures. Intermediates y and z were prepared intermediates using method F.

Intermediate y, 1-(1-bromoethyl)-4-(1-indanyl)benzene

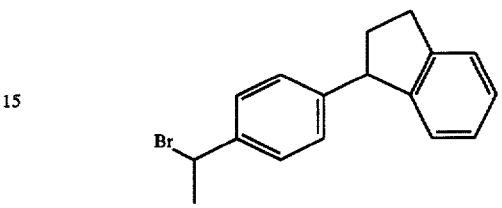

Intermediate z, 1-(1-bromoethyl)-4-(5-methoxy-1-indanyl) benzene

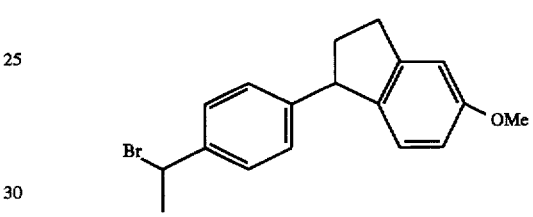

Example 16

Synthesis of Intermediate aa

A mixture of methyl 2-(bromomethyl)benzoate (10.00 g, 43.7 mmol), 4-(1-indanyl)phenol (11.47 g, 54.5 mmol), and potassium carbonate (13.27 g, 96.0 mmol) in DMF was heated at 60° C. for 4h, then was allowed to stir at room temperature for 3d. The resulting reaction mixture was partitioned between ether and water, then the organic phase was dried over magnesium sulfate, concentrated, and purified by chromatography over silica gel eluted with 4% ethyl acetate in hexanes to afford 14.8 g of methyl 2-[4-(1-indanyl)phenoxymethyl]benzoate as a colorless oil.

Excess aqueous 5% sodium hydroxide % was added to a solution of methyl 2-[4-(1-indanyl)phenoxymethyl] benzoate (14.7 g, 41.0 mmol) in dioxane. Reverse-phase HPLC showed complete reaction after stirring the reaction at room temperature overnight. Most of the dioxane was removed under vacuum and the residue was partitioned between ether and water. The organic phase was filtered and concentrated to a colorless oil which was crystallized by the addition of ether and hexanes. The solid was collected and washed with hexanes to afford 12.7 g of sodium 2-[4-(1-indanyl)phenoxymethyl]benzoyl as a white solid.

Oxalyl chloride (6.22 mL, 72.5 mmol) was added dropwise to a solution of of sodium 2-[4-(1-indanyl) phenoxymethyl]benzoate (12.56 g, 36.5 mmol) and catalytic DMF (2 drops) in methylene chloride. The resulting reaction was allowed to stir overnight at room temperature, then was concentrated under vacuum to afford 2-[4-(1-indanyl (phenoxymethyl]benzoyl chloride as a viscous yellow-orange oil.

A solution of 2-[4-(1-indanyl)phenoxymethyl]benzoyl chloride (12.56 g/34.6 mmol) in methylene chloride (100 mL) was added to a mixture of methoxylamine hydrochloride (4.34 g, 52.0 mmol) in aqueous 5% sodium hydroxide (50–100 mL) The organic phase was separated and washed with aqueous 5% HCl, then was dried over magnesium sulfate and concentrated to a solid. The solid was slurried in hexanes and collected to afford 6.84 g, of N-methoxy 2-[4-(1-indanyl)phenoxymethyl]benzamide as a white solid.

Carbon tetrachloride (2.54 mL, 25.6 mmol) was added dropwise to a solution of (N-methoxy 2-[4-(1-indanyl) phenoxymethyl]benzamide (6.54 g, 17.5 mmol) and triphenylphosphine (6.89 g, 26.3 mmol) in acetonitrile (100 mL). The resulting reaction mixture was refluxed for 1h, then was allowed to stir overnight at room temperature to give a black solution. This was concentrated, the solids were filtered off, and the filtrate was diluted with 5% ethyl acetate in hexanes. The additional solids which formed were filtered off, and the filtrate was concentrated to afford 6.8 g of a red oil which was purified by chromatography over silica gel eluted with 6% ethyl acetate/hexanes to afford 5.8 g of of N-methoxy 2-[4-(1-indanyl)phenoxymethyl]benzenecarboximidoyl chloride as a yellow oil.

Intermediate aa. N-methoxy-2-[4-(1-indanyl) phenoxymethyl]benzenecarboximidoyl chloride

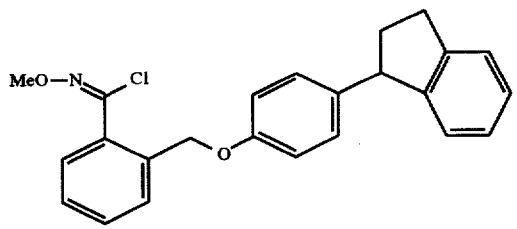

SYNTHESIS OF COMPOUNDS

Examples 17–54 illustrate the synthesis of compounds from the intermediates.

Example 17

Method G: Synthesis of Samples 1–7

A 60% oil dispersion of sodium hydride (1.1 equiv) was added to a solution of the oxime (1.0 equiv) from method C in DMF. The mixture was stirred at room temperature for 5 min, then methyl-(E)-2-(bromomethylphenyl)-2-methoxyiminoacetate (1.0 equiv) was added and the mixture was heated at 40° C. for 9h. The resulting mixture was diluted with ether and washed with water, then was dried over magnesium sulfate and purified by reverse phase chromatography.

Sample 1, Methyl 2-[[[[1-[4-(1-indanyl)phenyl] ethylidenyl]amino]oxy]-methyl]-α-methoxyimino phenylacetate

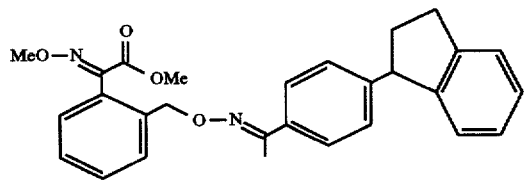

Intermediate g was reacted according to method G to give the Sample 1 as an oil. $^1$H NMR (CDCl$_3$) δ 7.6–7.5 (m, 3H), 7.4 (m, 2H), 7.3 (m, 1H), 7.2–7.1 (m, 5H), 6.9 (m, 1H, 5.1 (s, 2H), 4.4 (t, J=8 Hz, 1H), 4.1 (s, 3H), 3.8 (s, 3H) 3.1–2.9 (m, 2H), 2.6 (m, 1H), 2.2 (s, 3H), 2.1–2.0 (m, 1H).

Sample 2, Methyl 2-[[[[1-[4-(5-methoxy-1-indanyl) phenyl]ethylidenyl]amino]oxy]methyl]-α-methoxyimino phenylacetate

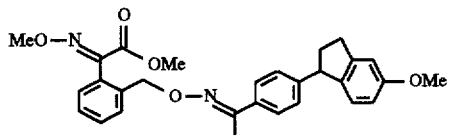

Intermediate h was reacted according to method G to give 100 mg (33%) of sample 2 as a colorless oil. $^1$H NMR (CDCl$_3$) δ 7.6–7.5 (m, 3H), 7.4 (m, 2H), 7.2 (m, 3H), 6.9–6.8 (m, 2H), 6.7 (m, 1H), 5.1 (s, 2H), 4.3 (t, J=8 Hz, 1H),4.1 (s, 3H), 3.8 (m, 6H), 3.1–2.9 (m, 2H), 2.6 (m, 1H), 2.2 (s, 3H), 2.1–2.0 (m, 1H).

Sample 3, Methyl 2-[[[[1-[4-(1-tetralinyl)phenyl] ethylidenyl]amino]oxy]-methyl]-α-methoxyimino phenylacetate

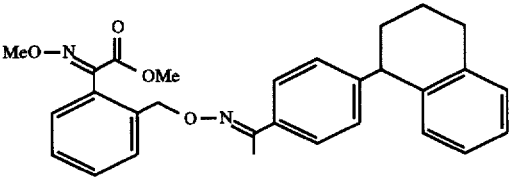

Intermediate i was reacted according to method G to give 90 mg (34%) of sample 3 as a colorless oil. $^1$H NMR (CDCl$_3$) δ7.5 (m, 3H), 7.4 (m, 2H), 7.2–7.0 (m, 6H), 6.8 (m, 1H), 5.1 (s, 2H), 4.1 (t, J=8 Hz, 1H), 4.0 (s, 3H), 3.8 (s, 3H), 3.8 (s, 3H), 3.0–2.8 (m, 2H), 2.2–2.1 (m, 4H), 1.9–1.7 (m, 3H).

Sample 4, Methyl 2-[[[[1-[4-(5-methoxy-1-tetralinyl)phenyl]ethylidenyl]-amino]oxy]methyl]-α-methoxyimino phenylacetate

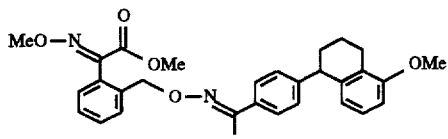

Intermediate j was reacted according to method G to give 120 mg (35%) of sample 4 as a colorless oil. $^1$H NMR (d$_6$-acetone) δ7.6–7.5 (m, 3H), 7.4 (m, 2H), 7.2 (m, 1H), 7.1 (m, 2H), 7.0 (m, 1H), 6.8 (m, 1H), 6.4 (m, 1H), 5.1 (s, 2H), 4.2 (t, J=8 Hz, 1H), 4.0 (s, 3H), 3.9 (s, 3H), 3.8 (s, 3H), 2.8–2.7 (m, 2H), 2.2 (s, 3H) 2.1 (m, 1H), 1.9–1.7 (m, 3H).

Sample 5. 2-[1-(methoxycarbonyl)methoxyiminomethyl]-3-[[[[1-[4-(1-indanyl)phenyl]ethylidenyl]amino]oxy]methyl]thiophene

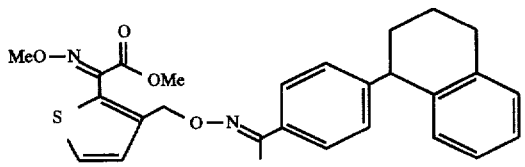

Intermediate g was reacted according to method G to give 100 mg (34%) of sample 5 as a colorless oil. $^1$H NMR (CDCl$_3$) δ 7.6 (m, 2H), 7.5 (m, 1H), 7.3 (m, 1H), 7.2–7.1 (m, 5H), 6.9 (m, 1H), 5.1 (s, 2H), 4.3 (t, J=8 Hz, 1H), 4.1 (s, 3H), 3.8 (s, 3H), 3.1–2.9 (m, 2H), 2.6–2.5 (m, 1H), 2.2 (s, 3H), 2.1–2.0 (m, 1H).

Sample 6. 2-[1-(methoxycarbonyl)methoxyiminomethyl]-3-[[[[1-[4-(1-tetralinyl)phenyl]ethylidenyl]amino]oxy]methyl]thiophene

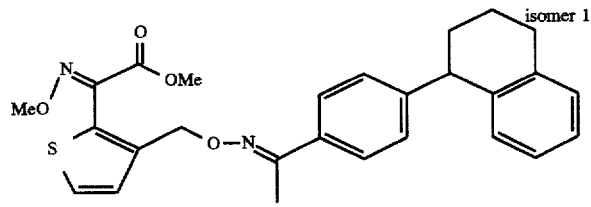

Intermediate i was reacted according to method G to give 110 mg (36%) of sample 6 as a colorless oil. $_1$H NMR (CDCl$_3$) δ 7.6–7.4 (m, 3H) 7.2–7.0 (m, 6H), 6.8 (m, 1H), 5.1 (s, 2H), 4.1 (m, 4H), 3.8 (s, 3H), 3.0–2.8 (m, 2H), 2.2–2.1 (m, 4H), 1.9–1.7 (m, 3H).

Sample 7. 2-[1-(methoxycarbonyl)methoxyiminomethyl]-3-[[[[1-[4-(1-tetralinyl)phenyl]ethylidenyl]amino]oxy]methyl]thiophene

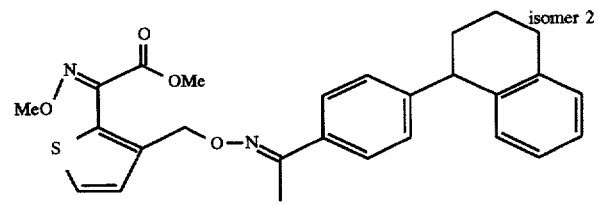

Intermediate i was reacted according to method G to give 110 mg (36%) of sample 7 as a colorless oil. $^1$H NMR (CDCl$_3$) δ 7.6 (m, 2H), 7.3 (m, 1H), 7.2–7.0 (m, 6H), 6.8 (m, 1H), 5.3 (s, 2H), 4.1 (t, J=8 Hz, 1H), 4.0 (s, 3H), 3.9 (s, 3H), 3.0–2.8 (m, 2H), 2.3 (s, 3H), 2.2 (m, 1H), 1.9–1.7 (m, 3H).

Example 18

Method H: Synthesis of Samples 8–16

A 1M solution of potassium tert-butoxide in THF (1.1 equiv) was added dropwise to a solution of either a substituted phenol (1.2 equiv) or alcohol (1.2 equiv) in THF. To this solution of potassium phenoxide or alkoxide was added a solution of methyl 2-bromomethyl phenyl-2-(methoxyimino)acetate (1.0 equiv) in THF. The resulting mixture was stirred at room temperature for 1d, then was partitioned between ether and water. The organic phase was dried over magnesium sulfate, concentrated, and purified by normal-phase or reverse-phase chromatography.

Sample 8. Methyl 2-[4-(5-chloro-1-indanyl)phenoxymethyl]-α-methoxyimino phenylacetate

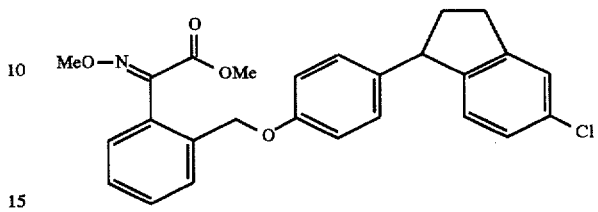

Intermediate k was reacted according to method H to give sample 8 as an oil. $^1$H NMR (CDCl$_3$) δ 7.6 (m, 1H), 7.5–7.4 (m, 2H), 7.3–7.2 (m, 2H), 7.1–7.0 (m, 3H), 6.9–6.8 (m, 3H), 5.0 (s, 2H), 4.2 (t, J=8 Hz, 1H), 4.0 (s, 3H), 3.8 (s, 3H), 3.1–2.8 (m, 2H), 2.6–2.5 (m, 1H), 2.1–2.0 (m, 1H).

Sample 9. Methyl 2-[4-(5-fluoro-1-indanyl)phenoxymethyl]-α-methoxyimino phenylacetate

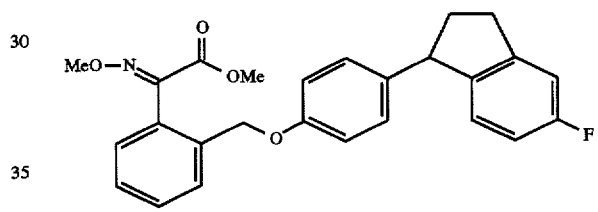

Intermediate l was reacted according to method H to give sample 9 as an oil. $^1$H NMR (CDCl$_3$) δ 7.5 (m, 1H), 7.4 (m, 2H), 7.2 (m, 1H), 7.1–7.0 (m, 2H), 6.9 (m, 1H), 6.8 (m, 4H), 4.9 (s, 2H), 4.2 (t, J=8 Hz, 1H), 4.0 (s, 3H), 3.8 (s, 3H), 3.0–2.8 (m, 2H), 2.6–2.5 (m, 1H), 2.0 (m, 1H).

Sample 10. Methyl 2-[4-(2-methyl-1-indanyl)phenoxymethyl]-α-methoxyimino phenylacetate

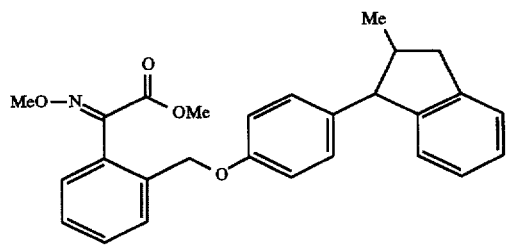

Intermediate m was reacted according to method H to give sample 10 as an oil. $^1$H NMR (CDCl$_3$) δ 7.6 (m, 1H), 7.5–7.4 (m, 2H), 7.3–7.1 (m, 5H), 6.9 (m, 2H), 6.8 (m, 2H), 4.9 (s, 2H), 4.3 (d, J=8 Hz, 1H), 4.0 (s, 3H), 3.8 (s, 3H), 3.1–3.0 (m, 1H), 2.9–2.6 (m, 2H), 0.7 (d, J=7 Hz, 3H).

Sample 11. Methyl2-[4-(3-methyl-1-indanyl) phenoxymethyl]-α-methoxyimino phenylacetate

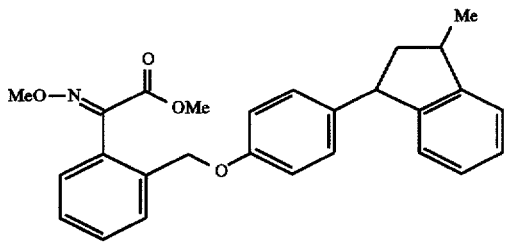

Intermediate n was reacted according to method H to give 107 mg of sample 11 as a white solid, mp 93.5°–97.5° C. ¹H NMR (CDCl₃) δ 7.6 (m, 1H), 7.5–7.3 (m, 2H), 7.2 (m, 3H), 7.1 (m, 3H), 6.8 (m, 3H), 4.9 (s, 2H), 4.2 (t, J=8 Hz, 1H), 4.0 (s, 3H), 3.8 (s, 3H), 3.2 (m, 1H), 2.7–2.6 (m, 1H), 1.6–1.5 (m, 1H), 1.4 (d, J=7 Hz, 3H).

Sample 12. Methyl 2-[4-(1-methyl-1-indanyl) phenoxymethyl]-α-methoxyimino phenylacetate

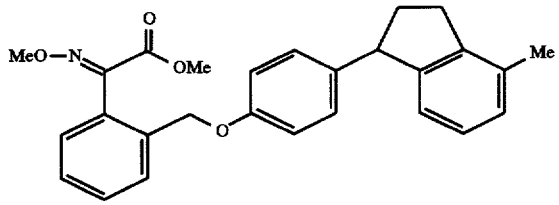

Intermediate o as reacted according to method H to give sample 12 as a solid, 108°–109.5° C. ¹H NMR (CDCl₃) δ 7.5 (m, 1H), 7.4 (m, 2H), 7.2 (m, 1H), 7.1–7.0 (m, 4H), 6.8 (m, 3H), 4.9 (s, 2H), 4.3 (t, J=8 Hz, 1H), 4.0 (s, 3H), 3.8 (s, 3H), 3.0–2.8 (m, 2H), 2.5 (m, 1H), 2.3 (s, 3H), 2.0 (m, 1H).

Sample 13. Methyl 2-[4-(1-methyl-1-indanyl) phenoxymethyl]-α-methoxyimino phenylacetate

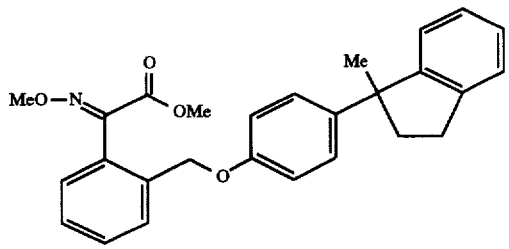

Intermediate p was reacted according to method H to give sample 13 as an oil. ¹H NMR of a mixture of isomers (CDCl₃) δ 7.5 (m, 1H), 7.4 (m, 2H), 7.3–7.0 (m, 7H), 6.8 (m, 2H), 4.9 (m, 2H), 4.0 (m, 3H), 3.8 (m, 3H), 2.9–1.8 (m, 4H), 1.6 (m, 3H).

Sample 14. Methyl 2-(1-indanoxymethyl)-α-methoxyimino phenylacetate

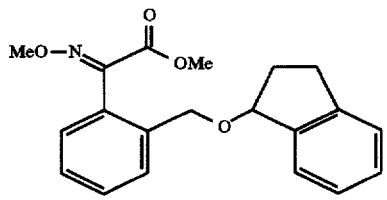

1-Indanol was reacted according to method H to give 55 mg (15%) of sample 14 as a white solid. ¹H NMR (CDCl₃) δ 7.50–7.48 (m, 1H), 7.43–7.32 (m, 3H), 7.25–7.14 (m, 4H), 4.91 (dd, J=6.5 Hz, 4.0 Hz, 1H), 4.49 (dd, J=14.7 Hz, 12.0 Hz, 12.0 , (2H), 4.00 (s, 3H), 3.77 (s, 3H), 3.14–3.04 (m, 1H), 2.84–2.72 (m, 1H), 2.34–2.23 (m, 1H), 2.14–2.04 (m, 1H).

Sample 15. Methyl 2-(2-indanoxymethyl)-α-methoxyimino phenylacetate

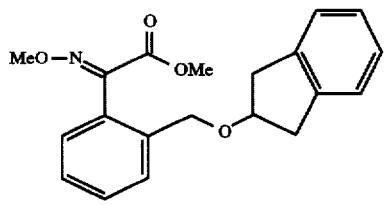

2-Indanol was reacted according to method H to give 58 mg (14%) of sample 15 as a yellow oil. ¹H NMR of a mixture of isomers (CDCl₃) δ 7.47–7.29 (m) and 7.22–7.12 (m, 8H combined), 5.69–5.60 (m) and 4.37–4.30 (m, 1H combined), 4.45 (s) and 4.29 (s, 2H combined), 4.03 (s) and 4.00 (s, 3H combined), 3.81 (s) and 3.21 (s, 3H combined), 3.42–3.34 (m) and 3.17–2.94 (m, 4H combined).

Sample 16. Methyl 2-(2-tetralinoxymethyl)-α-methoxyimino phenylacetate

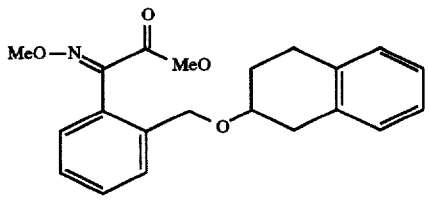

β-Tetralol was reacted according to method H to give 57 mg (15%) of sample 16 as a red oil. ¹H NMR of a mixture of isomers (CDCl₃) δ 7.48–7.27 (m) and 7.17–7.02 (m, 8H combined), 5.38–5.31 (m) and 3.80–3.70 (m, 1H combined), 4.51 (dd, J=12.2 Hz, 2.5 Hz) and 4.27 (s, 2H combined), 4.03 (s) and 4.02 (s, 3H combined), 3.83 (s) and 3.22 (s, 3H combined), 3.19–2.88 (m, 2H), 2.83–2.70 (m, 2H), 2.14–1.75 (m, 2H).

Example 19

Method I: Synthesis of Samples 17–26

A mixture of a 4-substituted phenol (1.0–1.5 equiv), methyl 2-bromomethyl phenyl-2-(methoxyimino)acetate (1.0 equiv) or methyl 3-bromomethyl-2-thienyl-2-(methoxyimino)acetate (1.0 equiv)), and potassium carbonate (2.0–2.2 equiv) in DMF was heated overnight at 60° C. The resulting mixture was cooled and partitioned between ether and water. The organic phase was dried over magnesium sulfate, concentrated, and purified by either recrystallization for ether/hexane mixtures or chromatography over silica gel eluted with ethyl acetate/hexane mixtures.

Sample 17. Methyl 2-[4-(1-indanyl)phenoxymethyl]-α-methoxyimino phenylacetate

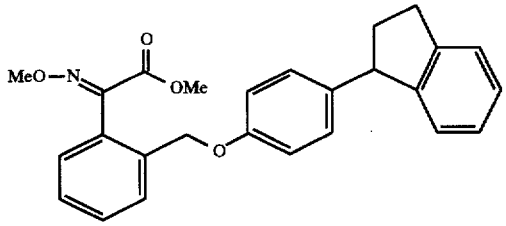

4-(1-Indanyl)phenol was reacted according to method I to give 1.71 g (58%) of sample 17 as a white solid. mp 86°–87° C. ¹H NMR (CDCl₃) δ 6.8–7.58 (m, 12H), 4.92 (s, 2H), 4.26 (t, 1H) 4.01 (s, 3H), 3.82 (s, 3H), 3.01 (m, 2H), 2.53 (m, 1H), 2.0 (m, 1H).

Sample 18. Methyl 2-[4-(1-tetalinyl)phenoxymethyl]-α-methoxyimino phenylacetate

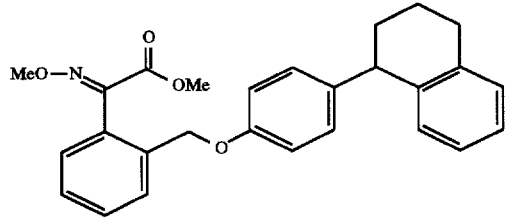

4-(1-Tetralinyl)phenol was reacted according to method I to give 90 mg (54%) of sample 18 as a white solid. mp 83°–85° C. ¹H NMR (CDCl₃) δ 7.5 (m, 1H), 7.4 (m, 2H), 7.2 (m, 1H), 7.1–6.9 (m, 5H), 6.8 (m, 3H), 4.9 (s, 2H), 4.1–4.0 (m, 4H), 3.8 (s, 3H), 2.9–2.8 (m, 2H), 2.2 (m, 1H), 1.9–1.7 (m, 3H).

Sample 19. Methyl 2-[4-(1-tetralinyl)-2-methyl phenoxymethyl]-α-methoxyimino phenylacetate

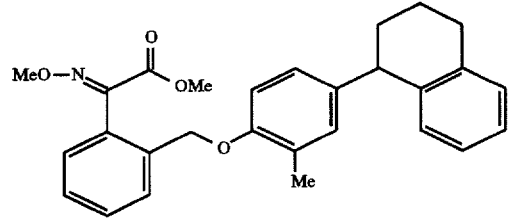

Intermediate q was reacted according to method I to give 80 mg (29%) of sample 19 as a white solid. mp 112°–114.5° C. ¹H NMR (CDCl₃) δ 7.6 (m, 1H), 7.5–7.3 (m, 2H), 7.2 (m, 1H), 7.1–7.0 (m, 3H), 6.9–6.8 (m, 3H), 6.7 (m,1H), 4.9 (s, 2H), 4.0 (m, 4H), 3.8 (s, 3H), 3.0–2.8 (m, 2H), 2.2 (s, 3H), 2.1 (m, 1H), 1.9–1.7 (m, 3H).

Sample 20. Methyl 3-[4-(1-indanyl)phenoxymethyl] thienyl-2-(α-methoxyimino acetate)

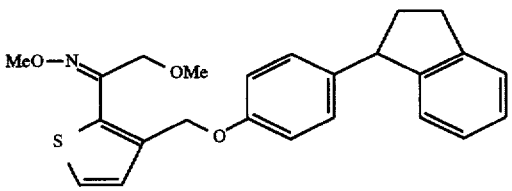

4-(1-Indanyl)phenol was reacted according to method I to give 200 mg (58%) of sample 20 as a yellow oil. ¹H NMR (CDCl₃) δ 7.5 (m, 1H), 7.3 (m, 1H), 7.2–7.0 (m, 5H), 6.9 (m, 1H), 6.8 (m, 2H), 4.9 (s, 2H), 4.3 (t, J=Hz, 1H), 4.1 (s, 3H), 3.8 (s, 3H), 3.1–2.9 (m, 2H), 2.6–2.5 (m, 1H), 2.0 (m, 1H).

Sample 21. Methyl 2-[4-(1-indanoxy) phenoxymethyl]-α-methoxyimino phenylacetate

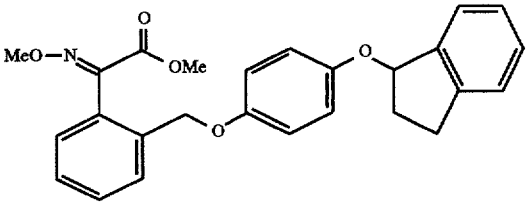

Intermediate r was reacted according to method to give 54 mg (51%) of compound 21 as a white solid. ¹H NMR (CDCl₃) δ 7.56–7.53 (d, 1H), 7.47–7.37 (m, 3H), 7.30–7.19 (m, 4H), 6.92–6.82 (symmetrical m, 4H), 5.67–5.64 (dd, J=6.7 Hz, 4.3 Hz, 1H), 4.91 (s, 2H), 4.03 (s, 3H), 3.84 (s, 3H), 3.18–3.08 (m, 1H), 2.95–2.85 (m, 1H), 2.56–2.45 (m, 1H), 2.25–2.14 (m, 1H).

Sample 22. Methyl 2-[4-(2-indanoxy) phenoxymethyl]-α-methoxyimino phenylacetate

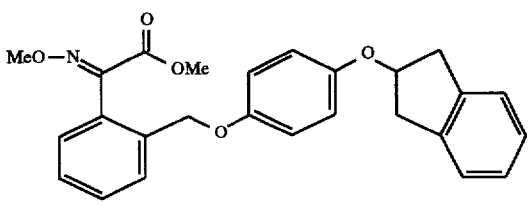

Intermediate s was reacted according to method I to give 60 mg (40%) of compound 22 as a white solid. ¹H NMR (CDCl₃) δ 7.55–7.52 (m, 1H), 7.46–7.36 (m, 2H), 7.26–7.16 (m, 5H), 6.81 (s, 4H), 5.08 (d oft, J=6.2 Hz, 3.1 Hz, 1H) 4.90 (s, 2H), 4.02 (s, 3H), 3.83 (s, 3H), 3.32 (dd, J=16.7 Hz, 6.2 Hz, 2H), 3.15 (dd, J=16.7 Hz, 3.1 Hz, 2H).

Sample 23, Methyl 2-[4-(2-tetralinoxy) phenoxymethyl]-α-methoxyimino phenylacetate

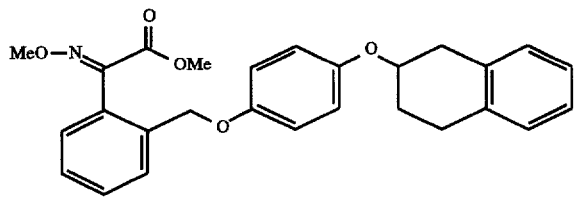

Intermediate t was reacted according to method I to give 96 mg (21%) of sample 23 as an oil. $^1$H NMR (CDCl$_3$) δ 7.55–7.54 (m, 1H), 7.46–7.37 (m, 2H), 7.22–7.20 (m, 1H), 7.15–7.07 (m, 4H), 6.88–6.81 (m, 4H), 4.91 (s, 2H), 4.63–4.57 (m, 1H), 4.03 (s, 3H), 3.84 (s, 3H), 3.20–3.14 (m, 1H), 3.05–2.94 (m, 2H), 2.88–2.80 (m, 1H), 2.19–2.12 (m, 1H), 2.06–1.96 (m, 1H).

Sample 24, Methyl 2-[3-(1-indanoxy) phenoxymethyl]-α-methoxyimino phenylacetate

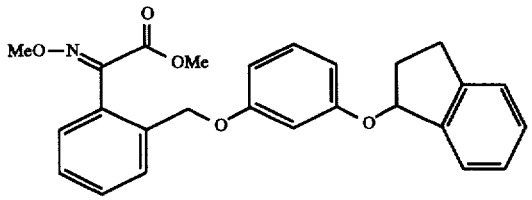

Intermediate u was reacted according to method I to give 149 mg (56%) of sample 24 as an oil. $^1$H NMR (CDCl$_3$) δ 7.55–7.14 (m, 9H), 6.63–6.50 (m, 3H), 5.72 (m, 1H), 4.92 (s, 2H), 4.01 (s, 3H), 3.81 (s, 3H), 3.17–3.09 (m, 1H), 2.94–2.87 (m, 1H), 2.57–2.48 (m, 1H), 2.22–2.14 (m, 1H).

Sample 25, Methyl 2-[3-(2-indanoxy) phenoxymethyl]-α-methoxyimino phenylacetate

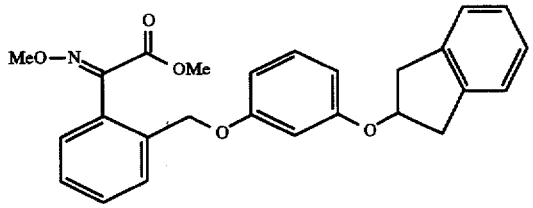

Intermediate v was reacted according to method I to give 200 mg (50%) of sample 25 as an oil. $^1$H NMR (CDCl$_3$) δ 7.57–7.54 (d, 1H), 7.47–7.36 (m, 2H), 7.27–7.15 (m, 6H), 6.58–6.38 (m, 3H), 5.16–5.11 (m, 1H), 4.94 (s, 2H), 4.02 (s, 3H), 3.83 (s, 3H), 3.41–3.31 (m, 2H), 3.22–3.14 (m, 2H).

Sample 26, Methyl 2-[3-(2-tetralinoxy) phenoxymethyl]-α-methoxyimino phenylacetate

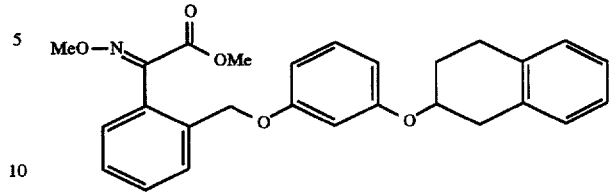

Intermediate w was reacted according to method I to give of sample 26 as an oil. $^1$H NMR (CDCl$_3$) δ 7.55–7.53 (m, 1H), 7.45–7.37 (m, 2H), 7.21–7.07 (m, 6H), 6.56–6.49 (m, 3H), 4.92 (s, 2H), 4.72–4.65 (m, 1H), 4.01 (s, 3H), 3.81 (s, 3H), 3.21–3.16 (m, 1H), 3.03–2.94 (m, 2H), 2.89–2.80 (m, 1H), 2.20–2.14 (m, 1H), 2.06–1.97 (m, 1H).

Example 20

Method J: Synthesis of Samples 27 and 28

A solution of methyl 2-[2-(chloromethyl)phenyl]-3-methoxypropenoate (1.0 equiv) and sodium iodide (1.5 equiv) in acetone was stirred at room temperature and monitored to completion by GC. The resulting mixture was filtered, concentrated under vacuum, then diluted with chloroform and filtered again to remove the remaining sodium salts. The filtrate was concentrated and purified by chromatography over silica gel eluted with ethyl acetate hexane mixtures to afford methyl 2-[2-(iodomethyl)phenyl]-3-methoxypropenoate as a yellow solid.

A mixture of methyl 2-[2-(iodomethyl)phenyl]-3-methoxypropenoate (1.2 equiv), a 4-substituted phenol (1.0 equiv), and potassium carbonate (2.3 equiv) in DMF was heated and stirred at 70° C. for 15h. The resulting reaction was cooled to room temperature and partitioned between ether and water, then the organic phase was washed with brine, then was dried over magesium sulfate and concentrated to an oil. This oil was dissolved in methylene chloride and reacted with the hydroxide form of an amberlite resin for 8h to remove the remaining 4-substituted phenol. The resin was filtered off and the methylene chloride solution was concentrated to afford product.

Sample 27, Methyl 2-[2-[4-(1-indanyl) phenoxymethyl]phenyl]-3-methoxypropenoate

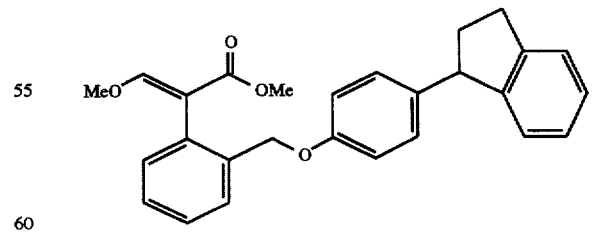

4-(1-Indanyl)phenol was reacted according to method J to give 103 mg (75%) of sample 27 as a yellow oil. $^1$H NMR (CDCl$_3$) δ 7.63 (s, 1H), 7.62–6.79 (m, 12H), 4.99 (s, 2H), 4.32 (t, J=11.2 Hz, 1H), 3.85 (s, 3H), 3.74 (s, 3H), 3.07–2.94 (m, 2H), 2.65–2.54 (m, 1H), 2.11–1.98 (m, 1H).

Sample 28. Methyl 2-[2-[4-(1-tetralinyl) phenoxymethyl]phenyl]-3-methoxypropenoate

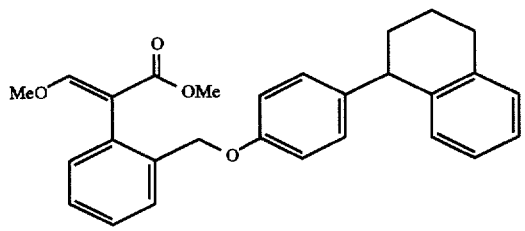

4-(1-Tetralinyl)phenol was reacted according to method J to give 113 mg (80%) of sample 28 as a pale yellow oil. $^1$H NMR (CDCl$_3$) δ 7.56 (m, 1H), 7.34–6.73 (m, 12H), 4.93 (s, 2H), 4.04 (t, J=6 Hz, 1H), 3.80 (s, 3H), 3.68 (s, 3H), 2.88–2.83 (m, 2H), 2.11 (m, 1H), 1.86–1.74 (m, 3H).

Example 21

Method K: Synthesis of Samples 29 and 30

A 60% oil dispersion of sodium hydride (1.1 equiv) was added to a solution of methyl 2-[(hydroxyimino)methyl]-α-(methoxyimino) phenylacetate in DMF. The mixture was stirred at room temperature for 5 min, then the bromide (1.0 equiv) from method F was added and the reaction stirred at 40° C. for 9h. This was partitioned between ether and water, then the organic phase was dried over magnesium sulfate, concentrated, and purified on a silica gel prep plate eluted with a mixture of ethyl acetate/hexanes.

Sample 29. Methyl 2-[[[[1-[4-(1-indanyl)phenyl] ethyl]oxy]imino]methyl]-α-(methoxyimino) phenylacetate

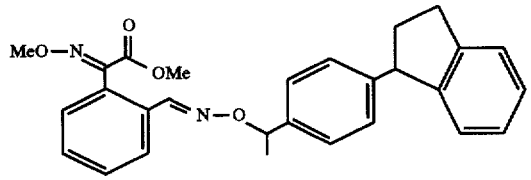

Intermediate y was reacted according to method K to give 100 mg (26%) of sample 29 as a colorless oil. $^1$H NMR (CDCl$_3$) δ 8.0 (s, 1H), 7.6 (m, 1H), 7.4 (m, 2H), 7.3–7.2 (m, 3H), 7.2–7.1 (m, 5H), 6.9 (m, 1H), 5.3 (q, J=7 Hz, 1H), 4.3 (t, J=8 Hz, 1H), 4.0 (s, 3H), 3.8 (s, 3H), 3.1–2.9 (m, 2H), 2.6–2.5 (m, 1H), 2.1–2.0 (m, 1H), 1.6 (d, J=7 Hz, 3H).

Sample 30. Methyl 2-[[[[1-[4-(5-methoxy-1-indanyl)phenyl]ethyl]oxy]imino]methyl]-α-(methoxyimino) phenylacetate

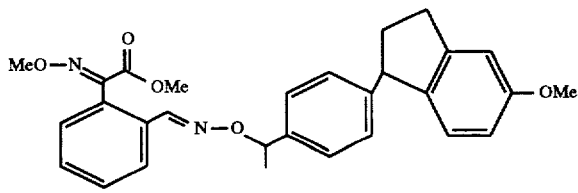

Intermediate z was reacted according to method K to give 300 mg (29%) of sample 30 as an oil. $^1$H NMR of a mixture of isomers (CDCl$_3$) δ 8.0 (s, 1H), 7.6 (m, 1H), 7.4 (m, 2H), 7.3 (m, 2H), 7.2 (m, 3H), 6.8 (m, 2H), 6.7 (m, 1H), 5.3 (m, 1H), 4.3 (t, J=8 Hz, 1H), 4.0 (m, 3H), 3.8 (m, 3H), 3.7 (m, 3H), 3.0–2.8 (m, 2H), 2.6–2.5 (m, 1H), 2.0 (m, 1H), 1.6 (m, 3H).

Example 22

Method L: Synthesis of Samples 31 and 32

A mixture of a 4-substituted phenol (1.25 equiv), (E)-methyl 2-[2-(6-chloropyrimidine-4-yloxy)phenyl]-3-methoxypropenoate (1.00 equiv), potassium carbonate (1.50 equiv), and catalytic copper(I) chloride in DMF was heated overnight at 95°–100° C. The resulting mixture was cooled and partitioned between ether and water. The organic phase was washed with aqueous 2N sodium hydroxide followed with brine, then was dried over magnesium sulfate, concentrated, and purified by chromatography over silica gel eluted with ethyl acetate/hexane mixtures.

Sample 31. Methyl 2-[2-[6-[4-(1-indanyl)phenoxy] pyrimidin-4-yloxy]phenyl]-3-methoxypropenoate

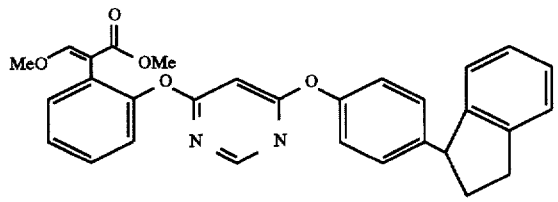

4-(1-Indanyl)phenol was reacted according to method L to give 160 mg (51%) of sample 31 as a white solid; $^1$H NMR (CDCl$_3$) δ 8.4 (s, 1H), 7.5 (s, 1H), 7.4–7.1 (m, 9H), 7.1–6.9 (m, 3H), 6.2 (s, 1H), 4.4 (t, J=8 Hz, 1H), 3.7 (s, 3H),3.6 (s, 3H), 3.1–2.9 (m, 2H), 2.6 (m, 1H), 2.1–2.0 (m, 1H).

Sample 32. Methyl 2-[2-[6-[4-(1-tetralinyl) phenoxy]pyrimidin-4-yloxy]phenyl]-3-methoxypropenoate

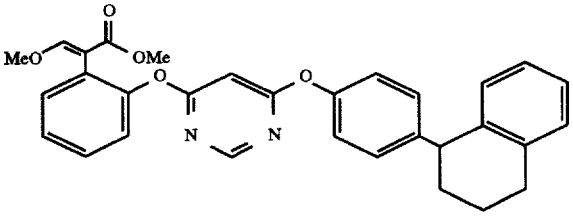

4-(1-Tetralinyl)phenol was reacted according to method L to give 132 mg (42%) of sample 32 as a white solid. $^1$H NMR (CDCl$_3$) δ 8.4 (s, 1H), 7.5 (s, 1H), 7.4–7.3 (m, 3H), 7.2–7.1 (m, 5H), 7.1–7.0 (m, 3H), 6.9 (m, 1H), 6.2 (s, 1H), 4.2 (t, J=7 Hz, 1H), 3.7 (s, 3H), 3.6 (s, 3H), 3.0–2.8 (m, 2H), 2.2 (m, 1H), 1.9–1.7 (m, 3H).

Example 23

Method M: Synthesis of Samples 33–51

Excess aqueous 40% methylamine (1 mL, 200 equiv) was added to a solution of an ortho-substituted methyl α-(methoxyimino) phenylacetate (20–30 mg) in THF. After stirring at 40° C. overnight, the volatile components were removed under vacuum and the residue was partitioned between ethyl acetate and brine. The organic layer was dried over magnesium sulfate and purified on a silica gel prep plate with a 3:7 ethyl acetate/hexane solution.

Sample 33. N-Methyl-2-[[[[1-[4-(1-indanyl)phenyl]ethylidenyl]amino]oxy]methyl]-α-methoxyimino benzeneacetamide

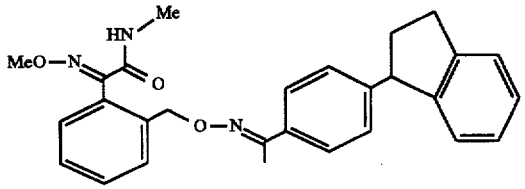

The compound of sample 1 was reacted according to method M to give sample 33 as an oil. ¹H NMR (CDCl₃) δ 7.6–7.5 (m, 3H), 7.4 (m, 2H), 7.3 (m, 1H), 7.2–7.1 (m, 5H), 6.9 (m, 1H), 6.7 (m, 1H), 5.1 (s, 2H), 4.4 (t, J=8 Hz, 1H), 4.0 (s, 3H), 3.1–2.8 (m, 5H), 2.6 (m, 1H), 2.2 (s, 3H), 2.1–2.0 (m, 1H).

Sample 34. N-Methyl-2-[[[[1-[4-(5-methoxy-1-indanyl)phenyl]ethylidenyl]amino]oxy]methyl]-α-methoxyimino benzeneacetamide

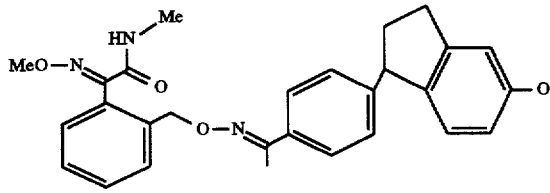

The compound of sample 2 was reacted according to method M to give 20 mg (67%) of sample 34 as a white solid. ¹H NMR (CDCl₃) δ 7.6–7.5 (m, 3H), 7.4 (m, 2H), 7.2 (m, 3H), 6.8 (m, 2H), 6.7–6.6 (m, 2H), 5.1 (s, 2H), 4.3 (t, J=8 Hz, 1H), 3.9 (s, 3H), 3.8 (s, 3H), 3.1–2.8 (m, 5H), 2.6 (m, 1H), 2.2 (s, 3H), 2.1–2.0 (m, 1H).

Sample 35. N-Methyl-2-[[[[1-[4-(1-tetralinyl)phenyl]ethylidenyl]amino]oxy]methyl]-α-methoxyimino benzeneacetamide

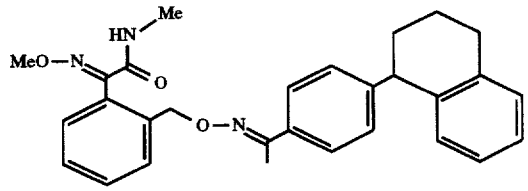

The compound of sample 3 was reacted according to method M to give 27 mg (77%) of sample 35 as a colorless oil. ¹H NMR (CDCl₃) δ 7.5 (m, 3H), 7.4 (m, 2H), 7.2–7.0 (m, 6H), 6.8 (m, 1H), 6.7 (m, 1H), 5.1 (s, 2H), 4.1 (t, J=8 Hz, 1H), 3.9 (s, 3H), 3.0–2.8 (m, 5H), 2.2–2.1 (m, 4H), 1.9–1.7 (m, 3H).

Sample 36. N-Methyl-2-[[[[1-[4-(5-methoxy-1-tetralinyl)phenyl]ethylidenyl]amino]oxy]methyl]-α-methoxyimino benzeneacetamide

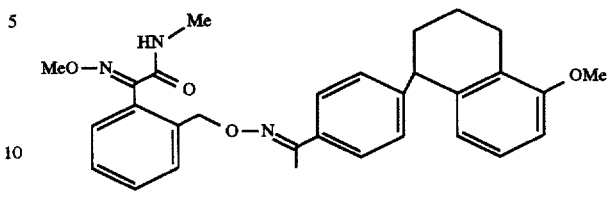

The compound of sample 4 was reacted according to method M to give 25 mg (83%) of sample 36 as a colorless oil. ¹H NMR (d₆-acetone) δ 7.6 (m, 2H), 7.5 (m, 1H), 7.4–7.3 (m, 2H), 7.2 (m, 1H), 7.1 (m, 2H), 7.0 (m, 1H), 6.8 (m, 1H), 6.4 (m, 1H), 5.1 (s, 2H), 4.1 (t, J=8 Hz, 1H), 3.9 (s, 3H), 3.8 (s, 3H), 2.8 (d, J=5 Hz, 3H), 2.7 (m, 2H), 2.2 (s, 3H), 2.1 (m, 1H), 1.9–1.7 (m, 3H).

Sample 37. N-Methyl-3-[[[[1-[4-(1-indanyl)phenyl]ethylidenyl]amino]oxy]methyl]-α-methoxyimino-2-thiopheneacetamide

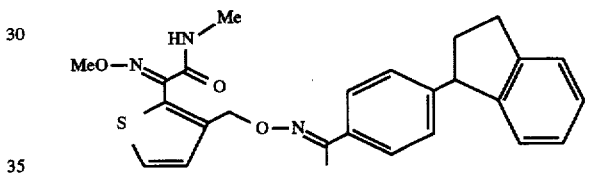

The compound of sample 5 was reacted according to method M to give 20 mg (80%) of sample 37 as a solid. ¹H NMR (CDCl₃) δ7.6 (m, 2H), 7.5 (m, 1H), 7.3 (m, 1H), 7.2–7.1 (m, 5H), 6.9 (m, 1H), 6.7 (m, 1H), 5.1 (s, 2H), 4.3 (t, J=8 Hz, 1H), 4.0 (s, 3H), 3.1–2.8 (m, 5H), 2.6 (m, 1H), 2.2 (s, 3H), 2.1–2.0 (m, 1H).

Sample 38. N-Methyl-3-[[[[1-[4-(1-tetralinyl)phenyl]ethylidenyl]amino]oxy]methyl]-α-methoxyimino-2-thiopheneacetamide

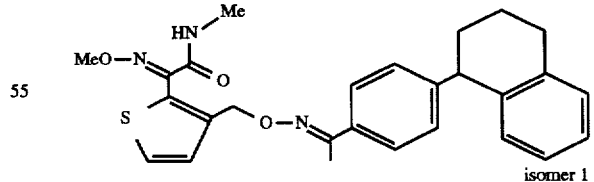

The compound of sample 6 was reacted according to method M to give 15 mg (75%) of sample 38 as a colorless oil. ¹H NMR (CDCl₃) δ 7.6–7.4 (m, 3H), 7.2–7.0 (m, 6H), 6.8 (m, 1H), 6.7 (m, 1H), 5.1 (s, 2H), 4.1 (t, J=8 Hz, 1H), 4.0 (s, 3H), 3.0–2.8 (m, 5H), 2.2–2.1 (m, 4H), 1.9–1.7 (m, 3H).

Sample 39, N-Methyl-3-[[[[1-[4-(1-tetralinyl)phenyl]ethylidenyl]amino]oxy]methyl]-α-methoxyimino-2-thiopheneacetamide

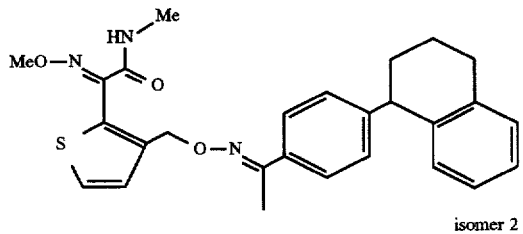

isomer 2

The compound of sample 7 was reacted according to method M to give 15 mg (75%) of sample 39 as a colorless oil. $^1$H NMR (CDCl$_3$) δ 7.5 (m, 2H), 7.3 (m, 1H), 7.2–7.0 (m, 6H), 6.8 (m, 1H), 6.4 (m, 1H), 5.3 (s, 2H), 4.1 (t, J=8 Hz, 1H), 4.0 (s, 3H), 3.0–2.8 (m, 5H), 2.2 (s, 3H), 2.1 (m, 1H), 1.9–1.7 (m, 3H).

Sample 40, N-Methyl-2-[4-(5-chloro-1-indanyl)phenoxymethyl]-α-methoxyimino benzeneacetamide

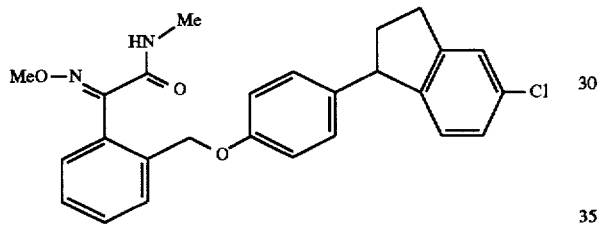

The compound of sample 8 was reacted according to method M to give 25 mg (83%) of sample 40 as a white solid. $^1$H NMR (CDCl$_3$) 7.6 (m, 1H), 7.5–7.4 (m, 2H), 7.3–7.2 (m, 2H), 7.1–7.0 (m, 3H), 6.9–6.8 (m, 3H), 6.7 (m, 1H), 4.2 (t, J=8 Hz, 1H), 4.0 (s, 3H), 3.1–2.8 (m, 5H), 2.6–2.5 (m, 1H), 2.1–2.0 (m, 1H).

Sample 41, N-Methyl-2-[4-(5-fluoro-1-indanyl)phenoxymethyl]-α-methoxyimino benzeneacetamide

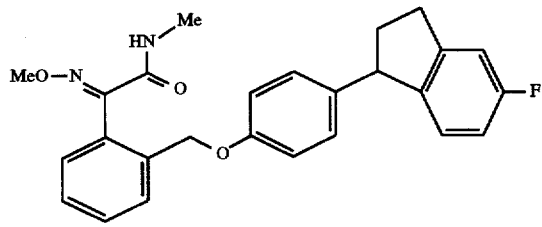

The compound of sample 9 was reacted according to method M to give 20 mg (80%) of sample 41 as a colorless oil. $^1$H NMR (CDCl$_3$) δ 7.5 (m, 1H), 7.4 (m, 2H), 7.2 (m, 1H), 7.0 (m, 2H), 6.9 (m, 1H), 6.8 (m, 4H), 6.7 (m, 1H), 4.9 (s, 2H), 4.2 (t, J=8Hz, 1H), 4.0 (s, 3H), 3.0–2.8 (m, 5H), 2.6–2.5 (m, 1H), 2.0 (m, 1H). Sample 42, N-Methyl-2-[4-(2-methyl-1-indanyl)phenoxymethyl]-α-methoxyiminobenzeneacetamide

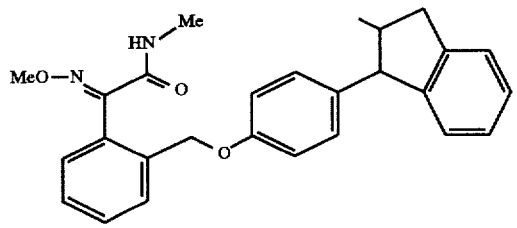

The compound of sample 10 was reacted according to method M to give 15 mg (75%) of sample 42 as a white solid. $^1$H NMR (CDCl$_3$) δ 7.6 (m, 1H), 7.5–7.4 (m, 2H), 7.3–7.1 (m, 5H), 6.9 (m, 2H), 6.8 (m, 2H), 6.7 (m, 1H), 4.9 (s, 2H), 4.3 (d, J=8 Hz, 1H), 4.0 (s, 3H), 3.1–3.0 (m, 1H), 2.9 (d, J=5 Hz, 3H), 2.8–2.6 (m, 2H), 0.7 (d, J =7 Hz, 3H).

Sample 43, N-Methyl-2-[4-(3-methyl-1-indanyl)phenoxymethyl]-α-methoxyimino benzeneacetamide

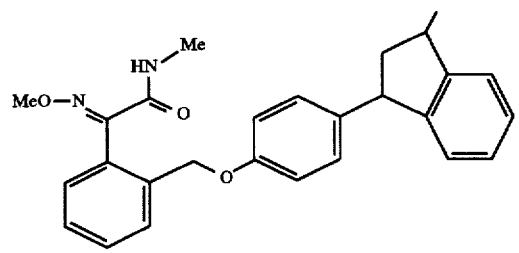

The compound of sample 11 was reacted according to method M to give 25 mg (83%) of sample 43 as a white solid. $^1$H NMR (CDCl$_3$) δ 7.57–7.55 (m, 1H), 7.45–7.40 (m, 2H), 7.28–7.23 (m, 3H), 7.16–7.13 (m, 3H), 6.90–6.86 (m, 3H), 6.72–6.71 (m, 1H), 4.97 (s, 2H), 4.23–4.16 (m, 1H), 3.96 (s, 3H), 3.26–3.14 (m, 1H), 2.91 (d, J=5 Hz, 3H), 2.71 (d of t, J=6.0 Hz, 12.1 Hz, 1H), 1.61 (q, J=11.9 Hz, 1H), 1.40 (d, J=7 Hz, 3H).

Sample 44, N-Methyl-2-[4-(4-methyl-1-indanyl)phenoxymethyl]-α-methoxyimino benzeneacetamide

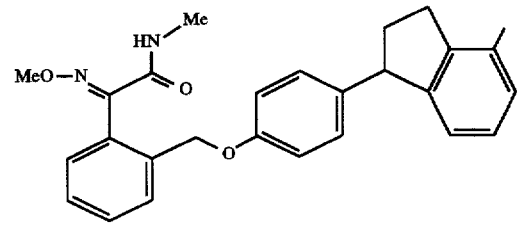

The compound of sample 12 was reacted according to method M to give 25 mg (83%) of sample 44 as a white solid, mp 136°–138.5° C. $^1$H NMR (CDCl$_3$) δ 7.5 (m, 1H), 7.4 (m, 2H), 7.2 (m, 1H), 7.1–7.0 (m, 4H), 6.9–6.8 (m, 3H), 6.7 (m,1H), 4.9 (s, 2H), 4.3 (t, J=8 Hz, 1H), 4.0 (s, 3H), 3.1–2.8 (m, 5H), 2.6 (m, 1H), 2.3 (s, 3H), 2.1–2.0 (m, 1H).

Sample 45. N-Methyl-2-[4-(1-methyl-1-indanyl)phenoxymethyl]-α-methoxyimino benzeneacetamide

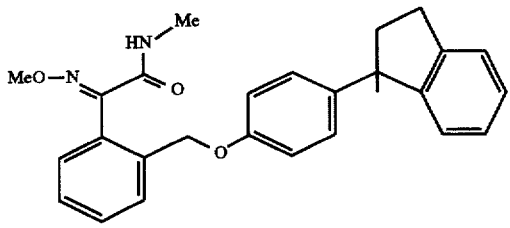

The compound of sample 13 was reacted according to method M to give sample 45 as an oil. ¹H NMR as a mixture of isomers (CDCl₃) δ 7.5 (m, 1H), 7.4 (m, 2H), 7.3–7.0 (m, 7H), 6.8 (m, 2H), 6.7 (m, 1H), 4.9 (m, 2H), 3.9 (m, 3H), 3.0–1.8 (m, 7H), 1.6 (m, 3H).

Sample 46. N-Methyl-2-[4-(1-indanyl)phenoxymethyl]-α-methoxyiminobenzeneacetamide

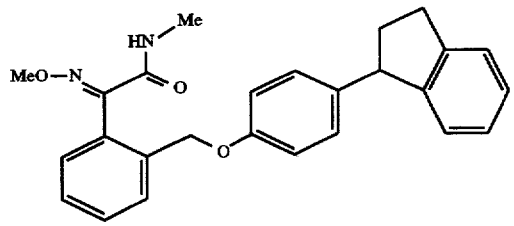

The compound of sample 17 was reacted according to method M to give 268 mg (67%) of sample 46 as a white solid, mp 96°–98° C. ¹H NMR (CDCl₃) δ 6.8–7.52 (m, 12H), 6.65 (s, 1H), 4.92 (s, 2H), 4.3 (t, 1H), 3.92 (s, 3H), 3.8–3.1 (m, 5H), 2.52 (m, 1H), 2.00 (m, 1H).

Sample 47. N-Methyl-2-[4-(1-tetralinyl)phenoxymethyl]-α-methoxyiminobenzeneacetamide

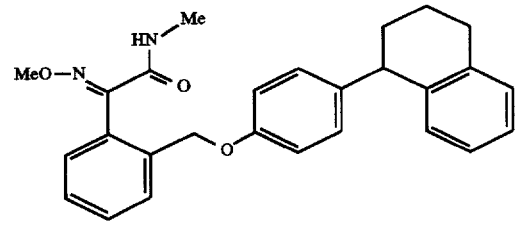

The compound of sample 18 was reacted according to method M to give 22 mg (88%) of sample 47 as a white solid, mp 118°–120° C. ¹H NMR (CDCl₃) δ 7.5 (m, 1H), 7.4 (m, 2H), 7.2 (m, 1H), 7.1–6.9 (m, 5H), 6.8 (m, 3H), 6.7 (m, 1H), 4.9 (s, 2H), 4.0 (t, J=7 Hz, 1H), 3.9 (s, 3H), 2.9–2.7 (m, 5H), 2.2 (m, 1H), 1.9–1.7 (m, 3H).

Sample 48. N-Methyl-2-[2-methyl-4-(1-tetralinyl)phenoxymethyl]-α-methoxyimino benzeneacetamide

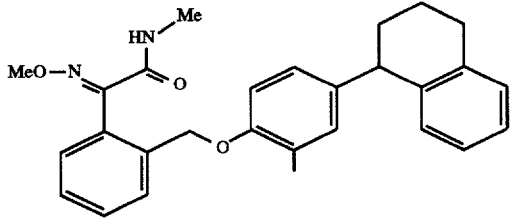

The compound of sample 19 was reacted according to method M to give sample 48. ¹H NMR (CDCl₃) δ 7.6 (m, 1H), 7.5–7.3 (m, 2H), 7.2 (m, 1H), 7.1–7.0 (m, 3H), 6.9–6.8 (m, 3H), 6.7 (m, 2H), 4.9 (s, 2H), 4.0 (t, J=7 Hz, 1H), 3.9 (s, 3H), 3.0–2.8 (m, 5H), 2.2 (s, 3H), 2.1 (m, 1H), 1.9–1.7 (m, 3H).

Sample 49. N-Methyl-3-[4-(1-indanyl)phenoxymethyl]-α-methoxyimino-2-thiopheneacetamide

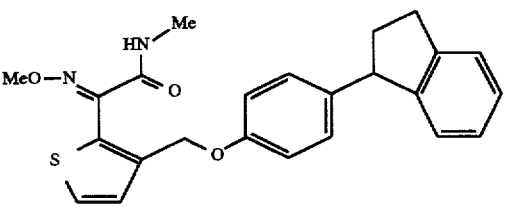

The compound of sample 20 was reacted according to method M to give 20 mg (80%) of sample 49 as a colorless oil. ¹H NMR (CDCl₃) δ 7.5 (m, 1H), 7.3 (m, 1H), 7.2–7.0 (m, 5H), 6.9 (m, 1H), 6.8 (m, 2H), 6.7 (m, 1H), 5.0 (s, 2H), 4.3 (t, J=8 Hz, 1H), 4.0 (s, 3H), 3.1–2.8 (m, 5H), 2.6–2.5 (m, 1H), 2.0 (m, 1H).

Sample 50. N-Methyl-2-[[[[1-[4-(1-indanyl)phenyl]ethyl]oxy]imino]methyl]-α-methoxyiminobenzeneacetamide

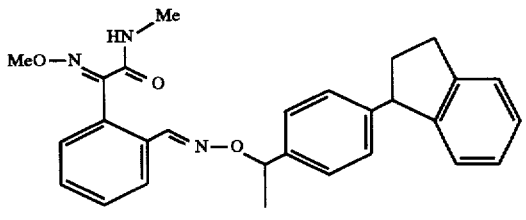

The compound of sample 29 was reacted according to method M to give 23 mg (77%) of sample 50 as a colorless oil. ¹H NMR (CDCl₃) δ 8.0 (s, 1H), 7.7 (m, 1H), 7.4 (m, 2H), 7.3–7.2 (m, 3H), 7.2–7.1 (m, 5H), 7.0 (m, 1H), 6.6 (m, 1H), 5.3 (q, J =7 Hz, 1H), 4.3 (t, J=8 Hz, 1H), 3.8 (s, 3H), 3.1–2.8 (m, 5H), 2.6–2.5 (m, 1H), 2.1–2.0 (m, 1H), 1.6 (d, J=7 Hz, 3H).

41

Sample 51, N-Methyl-2-[[[[1-[4-(5-methoxy-1-indanyl)phenyl]ethyl]oxy]imino]methyl]-α-methoxyimino benzeneacetamide

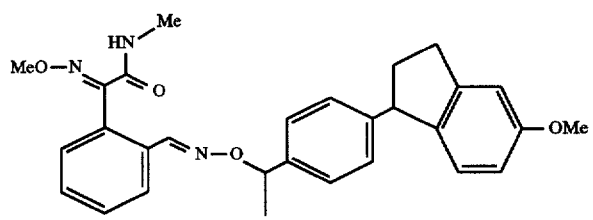

The compound of sample 30 as reacted according to method M to give sample 51. $^1$H NMR of a mixture of isomers (CDCl$_3$) δ 8.0 (s, 1H), 7.7 (m, 1H), 7.4 (m, 2H), 7.3 (m, 2H), 7.2 (m, 3H), 6.8 (m, 2H), 6.7 (m, 1H), 6.6 (m, 1H), 5.3–5.2 (m, 1H), 4.3 (t, J=8 Hz, 1H), 3.9 (m, 3H), 3.8 (m, 3H), 3.1–2.8 (m, 5H), 2.6–2.5 (m, 1H), 2.1–2.0 (m, 1H), 1.6 (m, 3H).

Example 24

Method N: Synthesis of Samples 52 and 53

A 60% oil dispersion of sodium hydride (2.0 equiv) was added to a solution of an azole (2.0 eq) in DMF, the mixture was stirred at room temperature for 10 min. N-methoxy 2-[4-(1-indanyl)phenoxymethyl]benzenecarboximidoyl chloride (intermediate aa, 1.0 equiv) was then added and the mixture was heated at 120° C. for 2h. The reaction was partitioned between ether and water. The organic phase was washed twice with 5% HCl, dried over magnesium sulfate, concentrated, and purified by chromatography over silica gel eluted with ethyl acetate/hexane mixtures.

Sample 52, N-[methoxyimino[2-[4-(1-indanyl)phenoxymethyl]phenyl]methyl]imidazole

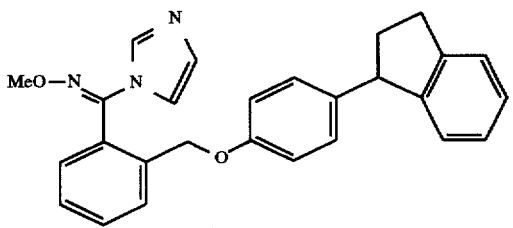

Imidazole was reacted according to method N to give 610 (48%) of sample 52 as a pale yellow oil. $^1$H NMR (CDCl$_3$) δ 8.12 (s, 1H), 7.66–7.63 (m, 1H), 7.56 (t, J =9 Hz, 1H), 7.46–7.07 (m, 9H), 6.96–6.92 (m, 1H), 6.77–6.72 (m, 2H), 5.02 (s, 2H), 4.29 (t, J=9 Hz, 1H), 3.98 (s, 3H), 3.10–2.90 (m, 2H), 2.61–2.5 (m, 1H), 2.09–1.96 (m, 1H).

42

Sample 53, 1-[methoxyimino[2-[4-(1-indanyl)phenoxymethyl]phenyl]methyl]-1,2,4-triazole

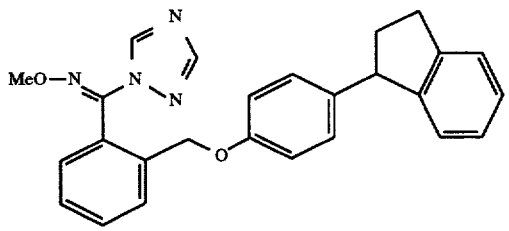

1,2,4-Triazole was reacted according to method N to give 850 mg (67%) of sample 53 as a yellow oil. $^1$H NMR (CDCl$_3$) δ 9.12 (s, 1H), 7.97 (s, 1H), 7.60–7.50 (m, 2H), 7.46 (m, 2H), 7.31–7.28 (m, 1H), 7.22–7.11 (m, 2H), 7.07 (d, J=8 Hz, 2H), 6.94 (d, J=8 Hz, 1H), 6.74 (d, J=8 Hz, 2H), 4.93 (s, 2H), 4.28 (t, J=8 Hz, 1H), 4.07 (s, 3H), 3.10–2.90 (m, 2H), 2.60–2.50 (m, 1H), 2.08–1.95 (m, 1H).

Example 25

Synthesis of Sample 54

A solution of methyl 2-[4-(1-indanyl)phenoxymethyl]-α-methoxyimino phenylacetate (sample 17, 80 mg) in excess 1-amino-2-propanol was heated at 120° C. for 12h. The resulting mixture was diluted with ethyl acetate and washed with water to remove most of the excess 1-amino-2-propanol. The ethyl acetate solution was then dried over magnesium sulfate, concentrated, and purified by reverse-phase chromatography to give 80 mg (88%) of sample 54 as an oil. $^1$H NMR (CDCl$_3$) δ 7.5 (m, 1H), 7.4 (m, 2H), 7.3–7.0 (m, 7H), 6.8 (m, 2H), 4.9 (s, 2H), 4.3 (t, J=8 Hz, 1H), 3.9 (s, 3H), 3.9 (m, 1H), 3.5 (m, 1H), 3.2 (m, 1H), 3.1–2.9 (m, 2H), 2.5 (m, 1H), 2.1 –2.0 (m, 1H), 1.2 (d, J=6 Hz, 3H).

Sample 54, N-(2-hydroxypropyl)-2-[4-(1-indanyl)phenoxymethyl]-α-methoxyimino benezeacetamide

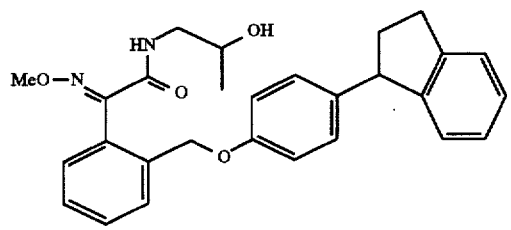

Example 26

Activity Table - Samples 1–54 and Standards

Samples 1–54 and commercial standards for the given disease were tested for their activity using the protocols described in Examples 1–6. The data appear in the Table below wherein "*" means that the stated value is is mean of more than one test and "–" indicates that no data is available.

| | In Vitro % Inhibition of Spore Germination | In Vivo % Disease Control | | | | |
|---|---|---|---|---|---|---|
| | *Microdochium* | Barley Powdery Mildew | | Wheat Glume Blotch | Wheat Leaf Rust | Vine Downy Mildew |
| Sample # | *nivale* @ 1.0/0.1 ppm (Example 1 protocol) | Protectant @ 20/5 ppm (Example 2 protocol) | Curative @ 20/5 ppm (Example 3 protocol) | protectant @ 20 ppm (Example 4 protocol) | protectant @ 20 ppm (Example 5 protocol) | protectant @ 20/5 ppm (Example 6 protocol) |
| 1 | 100/100 | 96*/66* | 90*/49* | 96 | 100* | 76/79 |
| 2 | 100/100 | 95*/61* | — | — | 100 | 71/51 |
| 3 | 100/98 | 98/58 | — | 74 | 100 | — |
| 4 | 100/99 | 73/53 | — | 44 | 100 | — |
| 5 | 100/100 | 56/20 | — | — | 100 | — |
| 6 | 100/100 | 73/38 | — | — | 89 | — |
| 7 | 100/99 | 74/37 | — | — | 58 | — |
| 8 | 100/100 | 65/48 | — | 23 | 98 | — |
| 9 | 100/100 | 49/51 | — | — | 98 | — |
| 10 | 100/100 | 43/13 | — | — | 100 | — |
| 11 | 100/95 | 39/35 | — | — | 97 | — |
| 12 | 100/100 | 61/41 | — | 29 | 100 | — |
| 13 | 100/100 | 39/20 | — | 35* | 98 | 41/55 |
| 14 | 100/69 | 12/7 | — | — | 66 | — |
| 15 | 83/10 | 0/16 | — | — | 68 | — |
| 16 | 100/47 | 6/0 | — | — | 20 | — |
| 17 | 100/100 | 78*/41* | 83*/56* | 93 | 98 | 86/73 |
| 18 | 100/100 | 73*/49* | — | 63 | 100 | — |
| 19 | 100/100 | 98/63 | 95/56 | — | 99 | — |
| 20 | 100/100 | 34/21 | — | — | 100 | — |
| 21 | 100/100 | 37/14 | — | — | 100 | — |
| 22 | 100/100 | 63/29 | — | — | 68 | — |
| 23 | 100/100 | 62/28 | — | — | 67 | — |
| 24 | 100/100 | 36/24 | — | — | 92 | — |
| 25 | 100/100 | 64/33 | — | — | 90 | — |
| 26 | 100/100 | 94/51 | — | — | 58 | — |
| 27 | 100/100 | 95/88* | — | — | 92 | 63/17 |
| 28 | 100/100 | 98/89* | — | — | 100 | 85/0 |
| 29 | 100/97 | 64/53 | 66/38 | 89 | 100 | — |
| 30 | 100/97 | 65/3 | — | — | 50 | — |
| 31 | 100/100 | 67/21 | — | — | 91 | — |
| 32 | 100/100 | 46/5 | — | — | 100 | — |
| 33 | 100/100 | 98*/81* | 92*/73* | 4 | 100* | 98*/72* |
| 34 | 100/100 | 98*/94* | 83/42 | — | 100 | 100/66 |
| 35 | 100/100 | 94/74 | 91/51 | — | 100 | — |
| 36 | 100/100 | 81/70 | — | 69 | 100 | — |
| 37 | 100/100 | 81/53 | — | — | 98 | — |
| 38 | 100/100 | 79/24 | — | — | 100 | — |
| 39 | 100/100 | 80/20 | — | — | 100 | — |
| 40 | 100/100 | 81/36 | — | 40 | 100 | — |
| 41 | 100/100 | 85/59 | — | 82 | 100 | — |
| 42 | 100/100 | 74/26 | — | 91 | 100 | — |
| 43 | 100/100 | 97*/74* | 82/48 | 70 | 100 | 94/45 |
| 44 | 100/97 | 79/52 | — | 47 | 100 | — |
| 45 | 100/100 | 44/9 | — | 48 | 100 | — |
| 46 | 100/100 | 97*/74* | 95*/78* | 99 | 100* | 100*/80* |
| 47 | 100/100 | 92*/64* | 80*/66* | 27 | 100 | 100/9 |
| 48 | 100/100 | 99*/93* | 93/88 | — | 100 | 78/41* |
| 49 | 100/98 | 44/32 | — | — | 98 | — |
| 50 | 99/100 | 87/68 | 97/59 | 96 | 98 | — |
| 51 | 100/97 | 89/56 | — | — | 100 | — |
| 52 | 96/48 | 19/6 | — | — | 0 | — |
| 53 | 10/6 | 3/0 | — | — | — | — |
| 54 | 98/9 | 7/8 | — | — | — | — |
| fenpiclonil | 88*/36* | | | | | |
| cyproconazole | | 96*/96* | 100*/98* | | | |
| tebuconazole | | | | 82* | 100* | |
| metalaxyl | | | | | | 66*/35* |

What is claimed is:

1. Compounds of Formula I:

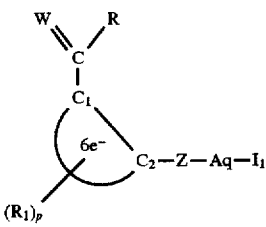

wherein $C_1$ and $C_2$ are carbon atoms which are part of an aromatic ring and are selected from the group consisting of phenyl and thienyl;

W is alkoxyimino, alkoxymethylene or alkylthiomethylene;

$R_1$ is independently selected from the group consisting of halogen, cyano, $C_1$-$C_4$ alkyl, $C_1$-$C_4$ alkoxy, wherein the alkyl or alkoxy are optionally substituted by halogen, and p is 0, 1, or 2;

Z is —$CH_2$—, —CH(OH)—, —CO—, —O—, —S—, —$NR_2$— wherein $R_2$ is hydrogen or a lower aliphatic group, —$CH_2CH_2$—, —CH=CH—,

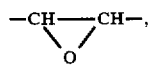

—$CH_2O$—, —$CH_2S$—, —$CH_2S(O)$—, —$OCH_2$—, —$SCH_2$—, —$S(O)CH_2$—, —$CH_2ON=C(R_3)$— or —CH=NB wherein B is —O—CO—, —N=$CR_3$, or —O—$CR_3R_4$— wherein $R_3$ and $R_4$ are independently hydrogen or $C_1$-$C_4$ alkyl optionally substituted by halogen;

A is an aromatic moiety having 1-2 aromatic rings connected linearly from Z to $I_1$ wherein the aromatic rings are optionally connected to each other and to $I_1$ in a linear manner with oxygen, nitrogen, or sulfur; wherein each aromatic ring is optionally independently substituted by $R_{10}$ groups; q is 1;

$I_1$ is:

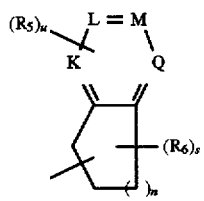

wherein

K, L, M, and Q are independently C or N with the proviso that not more than one or two of K, L, M or Q can be N at once and when K, L, M and Q are carbon each is optionally substituted by $R_5$;

n is 1 or 2; and each $R_5$ and $R_{10}$ group is independently selected from the group consisting of (a) halogen, (b) lower aliphatic group optionally substituted by halogen or $C_1$-$C_4$ alkoxy, (c) $C_1$-$C_4$ alkoxy optionally substituted by halogen, (d) —CN, (e) —$(Y_1)_{q_1}C(=X)(Y_2)_{q_2}R_8$, where; X is O or S, $q_1$ and $q_2$ are 0 or 1, $Y_1$ and $Y_2$ are independently selected from the group consisting of O, S, and —$NR_8$; each $R_8$ is independently selected from the group consisting of hydrogen and a lower aliphatic group optionally substituted by halogen or a $C_1$-$C_4$ alkoxy group, wherein $R_8$ cannot be hydrogen if both $q_1$ and $q_2$ are 1 and $Y_2$ is O or S; (f) —$S(O)_rR_9$ where r is 0, 1, or 2, wherein $R_9$ is a lower aliphatic group optionally substituted by halogen or a $C_1$-$C_4$ alkoxy group or $R_9$ is an aryl group optionally substituted by halogen, a $C_1$-$C_4$ alkoxy group, or a $C_1$-$C_4$ alkyl group, (g) —$Si(R_9)_3$, (h) —C(=$NOCH_3$)$CH_3$, or (i) aryl, aryloxy, arylthio, and arylamino optionally substituted by halogen, $C_1$-$C_4$ alkoxy, or a lower aliphatic group optionally substituted by halogen or $C_1$-$C_4$ alkoxy, u is an integer from 0 to 4

$R_6$ is halogen, hydroxy, $C_1$-$C_4$ alkoxy, or a lower aliphatic group, optionally substituted with $C_1$-$C_4$ alkoxy or halogen; s is 0, 1, or 2; and R is:

wherein

X is S or O;

Y is a bond, oxygen, sulfur, or nitrogen carrying a hydrogen, a $C_1$-$C_4$ alkyl group or a $C_1$-$C_4$ alkoxy group;

each $R_7$ is independently selected from the group consisting of hydrogen, and a lower aliphatic group optionally substituted by halogen, hydroxy, or a $C_1$-$C_4$ alkoxy group;

or an agronomically acceptable salt thereof.

2. The compound of claim 1 wherein W is alkoxyimino.

3. The compound of claim 2 wherein R is

wherein X and Y are oxygen atoms and $R_7$ is methyl.

4. The compound of claim 2 wherein $C_1$ and $C_2$ form a phenyl group.

5. The compound of claim 4 wherein Z is —$CH_2ON=C(R_3)$—.

6. The compound of claim 5 wherein q=1, A is phenyl, and $R_3$ is methyl.

7. The compound of claim 6 wherein K, L, M, and Q are carbon atoms and n=1.

8. The compound of claim 6 wherein K, L, M, and Q are carbon atoms and n=1.

9. The compound of claim 4 wherein Z is —$CH_2O$—.

10. Compounds of Formula I:

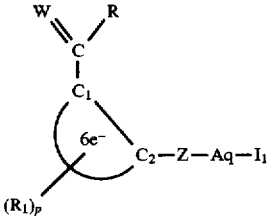

wherein $C_1$ and $C_2$ are carbon atoms which are part of an aromatic ring and are selected from the group consisting of phenyl and thienyl;

W is alkoxyimino;

$R_1$ is independently selected from the group consisting of halogen, cyano, $C_1$-$C_4$ alkyl, $C_1$-$C_4$ alkoxy, wherein the alkyl or alkoxy are optionally substituted by halogen, and p is 0;

Z is —O—, —CH$_2$O—, CH$_2$ON=C(R$_3$)— or —CH=NB wherein B is —O—CR$_3$R$_4$— wherein R$_3$ is methyl and R$_4$ is hydrogen;

A is an aromatic moiety having 1 aromatic ring connected linearly from Z to I$_1$ wherein the aromatic ring is optionally connected to I$_1$ in a linear manner with oxygen wherein the aromatic ring is optionally substituted by a C$_1$-C$_4$ alkyl group; q is 1;

I$_1$ is:

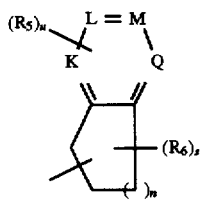

wherein

K, L, M and Q are C, and each is optionally substituted by R$_5$;

n is 1 or 2; and each R$_5$ group is independently selected from the group consisting of (a) halogen, (b) lower aliphatic group, and (c) C$_1$-C$_4$ alkoxy;

u is 0 or 1;

R$_6$ is a lower aliphatic group; s is 0 or 1; and

R is:

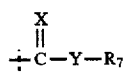

wherein X is O;

Y is oxygen or nitrogen carrying a hydrogen;

each R$_7$ is a lower aliphatic group optionally substituted by hydroxy; or an agronomically acceptable salt thereof.

11. A compound of claim 10 wherein said aromatic ring is phenyl.

12. A compound of claim 11 wherein said aromatic ring is thienyl.

13. The compound of claim 9 wherein q=1 and A is phenyl.

14. The compound of claim 13 wherein K, L, M, and Q are carbon atoms and n=1.

15. The compound of claim 13 wherein K, L, M, and Q are carbon atoms and n=2.

16. The compound of claim 9 wherein q=1 and A is phenoxy.

17. The compound of claim wherein K, L, M, and Q are carbon atoms and n=1.

18. The compound of claim 17 wherein K, L, M, and Q are carbon atoms and n=2.

19. The compound of claim 4 wherein Z is —CH=NB.

20. The compound of claim 19 wherein q=1, A is phenyl, and B is —OCR$_3$R$_4$ wherein R$_3$ is hydrogen and R$_4$ is methyl.

21. The compound of claim 20 wherein K, L, M, and Q are carbon atoms and n=1.

22. The compound of claim 3 wherein C$_1$ and C$_2$ form a thienyl group.

23. The compound of claim 22 wherein Z is —CH$_2$ON=C(R$_3$)—.

24. The compound of claim 23 wherein q=1, A is phenyl, and R$_3$ is methyl.

25. The compound of claim 24 wherein K, L, M, and Q are carbon atoms and n=1.

26. The compound of claim 24 wherein K, L, M, and Q are carbon atoms and n=2.

27. The compound of claim 22 wherein Z is —CH$_2$O—.

28. The compound of claim 27 wherein q=1 and A is phenyl.

29. The compound of claim 28 wherein K, L, M, and Q are carbon atoms and n=1.

30. The compound of claim 2 wherein R is

wherein X is an oxygen atom, Y is an —NH— group, and R$_7$ is methyl.

31. The compound of claim 30 wherein C$_1$ and C$_2$ form a phenyl group.

32. The compound of claim 31 wherein Z is —CH$_2$ON=C(R$_3$)—.

33. The compound of claim 32 wherein q=1, A is phenyl, and R$_3$ is methyl.

34. The compound of claim 33 wherein K, L, M, and Q are carbon atoms and n=1.

35. The compound of claim 33 wherein K, L, M, and Q are carbon atoms and n=2.

36. The compound of claim 31 wherein Z is —CH$_2$O—.

37. The compound of claim 36 wherein q=1 and A is phenyl.

38. The compound of claim 37 wherein K, L, M, and Q are carbon atoms and n=1.

39. The compound of claim 37 wherein K, L, M, and Q are carbon atoms and n=2.

40. The compound of claim 31 wherein Z is —CH=NB.

41. The compound of claim 40 wherein q=1, A is phenyl, and B is —OCR$_3$R$_4$ wherein R$_3$ is hydrogen and R$_4$ is methyl.

42. The compound of claim 41 wherein K, L, M, and Q are carbon atoms and n=1.

43. The compound of claim 41 wherein K, L, M, and Q are carbon atoms and n n=2.

44. The compound of claim 30 wherein C$_1$ and C$_2$ form a thienyl group.

45. The compound of claim 44 wherein Z is —CH$_2$ON=C(R$_3$)—.

46. The compound of claim 45 wherein q=1, A is phenyl, and R$_3$ is methyl.

47. The compound of claim 46 wherein K, L, M, and Q are carbon atoms and n=1.

48. The compound of claim 46 wherein K, L, M, and Q are carbon atoms and n=2.

49. The compound of claim 44 wherein Z is —CH$_2$O—.

50. The compound of claim 49 wherein q=1 and A is phenyl.

51. The compound of claim 50 wherein K, L, M, and Q are carbon atoms and n=1.

52. The compound of claim 2 wherein R is

wherein X is an oxygen atom, Y is an —NH— group, and R$_7$ is a lower aliphatic group optionally substituted with —OH.

53. The compound of claim 52 wherein C$_1$ and C$_2$ form a phenyl group.

54. The compound of claim 53 wherein Z is —CH$_2$O—.

55. The compound of claim 54 wherein q=1 and A is phenyl.

56. The compound of claim 55 wherein K, L, M, and Q are carbon atoms and n=1.

57. The compound of claim 1 wherein W is alkoxymethylene.

58. The compound of claim 57 wherein R is

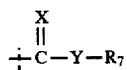   a)

wherein X and Y are oxygen atoms and R$_7$ is methyl.

59. The compound of claim 58 wherein C$_1$ and C$_2$ form a phenyl group.

60. The compound of claim 59 wherein Z is —CH$_2$O—.

61. The compound of claim 60 wherein q=1 and A is phenyl.

62. The compound of claim 61 wherein K, L, M, and Q are carbon atoms and n=1.

63. The compound of claim 61 wherein K, L, M, and Q are carbon atoms and n=2.

64. The compound of claim 59 wherein Z is —O—.

65. The compound of claim 64 wherein q=1 and A is pyrimidinyloxyphenyl.

66. The compound of claim 65 wherein K, L, M, and Q are carbon atoms and n=1.

67. The compound of claim 65 wherein K, L, M, and Q are carbon atoms and n=2.

68. The composition for use as a fungicide comprising a fungicidally effective amount of a compound of Formula I of claim 1 together with an agronomically acceptable carrier.

69. A method of using the compound of claim 1 as a fungicidal agent comprising treatment with an effective amount of a compound of claim 1.

* * * * *

UNITED STATES PATENT AND TRADEMARK OFFICE
CERTIFICATE OF CORRECTION

PATENT NO.   :   5,739,140

DATED        :   April 14, 1998

INVENTOR(S)  :   William P. Clinton et al.

It is certified that error appears in the above-identified patent and that said Letters Patent is hereby corrected as shown below:

Col. 47, line 44: delete "11" and insert --10--

Col. 47, line 54: after "claim" insert --16--

Col. 48, line 42: delete first occurrence of "n"

Signed and Sealed this

Twenty-third Day of June, 1998

Attest:

BRUCE LEHMAN

Attesting Officer    Commissioner of Patents and Trademarks